(12) United States Patent
Maduskuie

(10) Patent No.: US 7,101,883 B2
(45) Date of Patent: Sep. 5, 2006

(54) URACIL DERIVATIVES AS INHIBITORS OF TNF-α CONVERTING ENZYME (TACE) AND MATRIX METALLOPROTEINASES

(75) Inventor: Thomas P. Maduskuie, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 385 days.

(21) Appl. No.: 10/389,529

(22) Filed: Mar. 14, 2003

(65) Prior Publication Data

US 2003/0229081 A1    Dec. 11, 2003

Related U.S. Application Data

(60) Provisional application No. 60/365,334, filed on Mar. 18, 2002.

(51) Int. Cl.
*C07D 239/02* (2006.01)
*A01N 43/58* (2006.01)
*A61K 31/50* (2006.01)

(52) U.S. Cl. .................. 514/247; 544/224; 544/242
(58) Field of Classification Search .......... 514/247; 544/224, 242
See application file for complete search history.

(56) References Cited

U.S. PATENT DOCUMENTS

| 3,242,180 A | 3/1966 | Hitchings et al. |
| 4,722,929 A | 2/1988 | Austel et al. |
| 5,332,759 A | 7/1994 | Depreux et al. |
| 5,424,311 A | 6/1995 | Billhardt-Troughton et al. |
| 5,591,776 A | 1/1997 | Cavalla et al. |
| 6,242,455 B1 | 6/2001 | Grams et al. |

FOREIGN PATENT DOCUMENTS

| EP | 0 532 239 | 3/1993 |
| WO | WO 95/26957 | 10/1995 |
| WO | WO 99/32117 | 7/1999 |
| WO | WO 01/12611 | 2/2001 |
| WO | WO 01/74753 | 10/2001 |
| WO | WO 01/96308 | 12/2001 |

*Primary Examiner*—James O. Wilson
*Assistant Examiner*—Paul V. Ward
(74) *Attorney, Agent, or Firm*—Jing G. Sun

(57) ABSTRACT

The present application describes novel uracil derivatives of formula I:

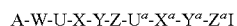

$$A\text{-}W\text{-}U\text{-}X\text{-}Y\text{-}Z\text{-}U^a\text{-}X^a\text{-}Y^a\text{-}Z^a \quad I$$

or pharmaceutically acceptable salt or prodrug forms thereof, wherein A, W, U, X, Y, Z, $U^a$, $X^a$, $Y^a$, and $Z^a$ are defined in the present specification, which are useful as inhibitors of TNF-α converting enzyme (TACE), matrix metalloproteinases (MMP), aggrecanase or a combination thereof.

18 Claims, No Drawings

URACIL DERIVATIVES AS INHIBITORS OF TNF-α CONVERTING ENZYME (TACE) AND MATRIX METALLOPROTEINASES

CROSS-REFERENCE TO RELATED APPLICATIONS

This application claims the priority benefit of U.S. Provisional Application No. 60/365,334, filed Mar. 18, 2002, the disclosure of which is incorporated herein by reference in its entirety.

FIELD OF THE INVENTION

This invention relates generally to novel uracil derivatives as inhibitors of TNF-α converting enzyme (TACE), matrix metalloproteinases (MMP), aggrecanase or a combination thereof, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis; corneal, epidermal, or gastric ulceration; tumor metastasis or invasion; periodontal disease; and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic, and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with the severity of the lesion (Mankin et al. *Arthritis Rheum.* 1978, 21, 761–766, Woessner et al. *Arthritis Rheum.* 1983, 26, 63–68, and Woessner et al. *Arthritis Rheum.* 1984, 27, 305–312). In addition, aggrecanase has been identified as providing the specific cleavage product of proteoglycan found in RA and OA patients (Lohmander L. S. et al. *Arthritis Rheum.* 1993, 36, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor-α (TNF-α) is a cell-associated cytokine that is processed from a 26kd precursor form to a 17kd soluble form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al, *Lancet* 1994, 344, 1105), non-insulin dependent diabetes melitus (Lohmander, L. S. et al. *Arthritis Rheum.* 1993, 36, 1214–22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV, and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

It is desirable to find new compounds with improved pharmacological characteristics compared with known MMP and/or TACE inhibitors. For example, it is preferred to find new compounds with improved MMP and/or TACE inhibitory activity and selectivity for an MMP and/or TACE versus other metalloproteases. It is also desirable and preferable to find compounds with advantageous and improved characteristics in one or more of the following categories: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

EP 532,239 discloses 5-lipoxygenase inhibitors of the following formula:

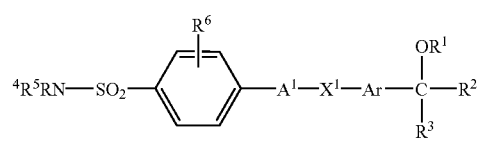

wherein $R^4$ can be a 6-membered monocyclic moiety containing 1–2 N; $R^5$ is H or (1–4C)alkyl; $A^1$ is a direct link or (1–3C)alkylene; $X^1$ is O, S or imino; Ar is optionally substituted phenylene; and $R^1$, $R^2$, and $R^3$ are groups as defined in EP 532,239.

WO 95/26957 describes endothelin receptor antagonists of the following formula:

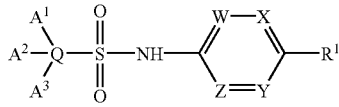

wherein Q is a naphthyl or biphenyl group; W, X, Y and Z are independently selected from N or $CR^2$; and $A^1$, $A^2$, $A^3$ and $R^1$ are groups as defined in WO 95/26957.

U.S. Pat. No. 5,332,759 describes compounds of the following formula:

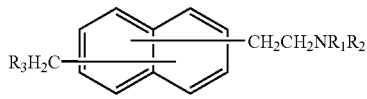

wherein $R_3$ is $-SO_2-NR_6R_7$ or $-CO-NR_6R_7$; $R_6$ and $R_7$ have the same definition as $R_1$ and $R_2$; and $R_1$ and $R_2$ are groups as defined in U.S. Pat. No. 5,332,759.

U.S. Pat. No. 5,424,311 discloses intermediates of the following formula:

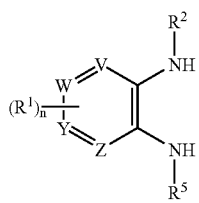

wherein V, W, Y and Z are $CR^1$ or N; $R^2$ and $R^5$ are groups as defined in U.S. Pat. No. 5,424,311.

WO99/32117 illustrates acetylcholine receptor modulators of the following formula:

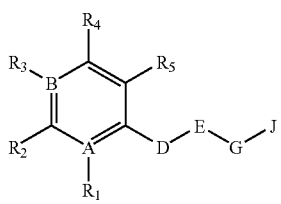

wherein A and B can be N; $R_1$ and $R_2$ can be H; D, E and G are linkers; J is $NR_cR_f$ as defined in WO99/32117; $R_5$ is $-OR_4$, $-OC(O)O-R_4$, $-SR_4$, $-NHC(O)R_4$, $-NHSO_2R_4$; and $R_4$ can be an optionally substituted aryl.

U.S. Pat. No. 6,242,455 depicts metalloproteinase inhibitors of the following formula:

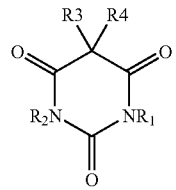

wherein $R_1$ and $R_2$ can be H; R3 is W-V; W is a linker; V is H or a ring; and R4 is a residue as defined in U.S. Pat. No. 6,242,455.

WO 01/12611 describes metalloproteinase inhibitors of the following formula:

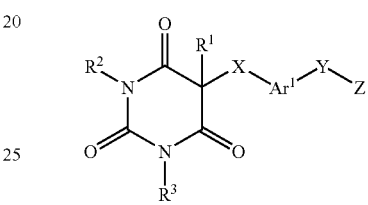

wherein X and Y are linkers; $Ar^1$ is $(C_6-C_{10})$aryl or $(C_2-C_{10})$ heteroaryl; and Z is $(C_6-C_{10})$aryl, $(C_3-C_8)$cycloalkyl, $(C_3-C_8)$cycloalkyl$(C_1-C_4)$alkyl or $(C_2-C_{10})$heteroaryl.

WO 01/96308 discloses AMPA receptor and kainite receptor inhibitors of the following formula:

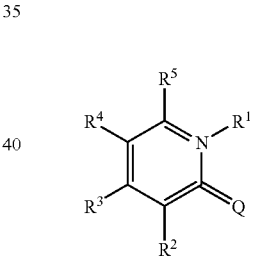

wherein Q is NH, O or S; and $R^1$ can be a dihydroxypyrimidyl capped group.

Compounds specifically described in the above mentioned patents or patent applications are not considered to be part of the present invention.

The compounds of the present invention act as inhibitors of MPs, in particular TACE, MMPs, and/or aggrecanase. These novel molecules are provided as anti-inflammatory compounds and cartilage protecting therapeutics.

SUMMARY OF THE INVENTION

Accordingly, the present invention provides novel uracil derivative compounds useful as MMP, TACE, and/or aggrecanase inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory disorders, comprising: administering to a mammal, in need of such treatment, a therapeutically effective amount of at least one of the compounds of the present invention or a pharmaceutically acceptable salt or prodrug form thereof.

The present invention provides a method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt or prodrug form thereof.

The present invention provides a method comprising: administering a compound of the present invention or a pharmaceutically acceptable salt or prodrug form thereof in an amount effective to treat a condition or disease mediated by MMPs, TACE, aggrecanase, or a combination thereof.

The present invention provides novel compounds of the present invention for use in therapy.

The present invention provides the use of novel compounds of the present invention for the manufacture of a medicament for the treatment of a condition or disease mediated by MMPs, TACE, aggrecanase, or a combination thereof.

The present invention provides a method for treating inflammatory disorders, comprising: administering, to a mammal in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

The present invention provides a medical device for implanting into a mammalian body wherein the medical device has a coating material comprising an amount of one of the compounds of the present invention or a pharmaceutically-acceptable salt, hydrate, or prodrug thereof, effective for reducing inflammation or restinosis. Preferably, the implantable medical device is a stent.

These and other objects, which will become apparent during the following detailed description, have been achieved by the inventors' discovery that compounds of formula I:

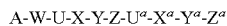

or pharmaceutically acceptable salt or prodrug forms thereof, wherein A, W, U, X, Y, Z, $U^a$, $X^a$, $Y^a$, and $Z^a$ are defined below, are effective TACE and matrix metalloproteinses inhibitors.

DETAILED DESCRIPTION OF PREFERRED EMBODIMENTS

[1] Thus, in an embodiment, the present invention provides a novel compound of formula I:

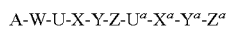

or a stereoisomer or pharmaceutically acceptable salt form thereof, wherein;

A is selected from the group:

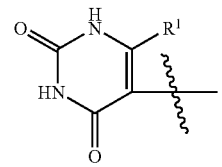

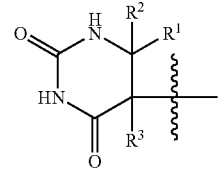

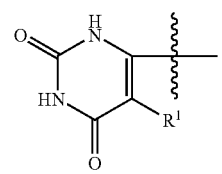

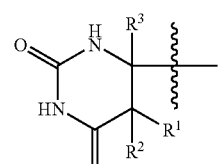

W is $(CHR^a)_m$;
U is absent or is selected from: O, $NR^{a1}$, C(O), $CR^a(OH)$, C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $OS(O)_2$, $S(O)_2O$, $S(O)_p$, $S(O)_pNR^{a1}$, $NR^{a1}S(O)_p$, and $NR^{a1}SO_2NR^{a1}$;
X is absent or is selected from $C_{1-3}$ alkylene, $C_{2-3}$ alkenylene, and $C_{2-3}$ alkynylene;
Y is absent or is selected from O, $NR^{a1}$, $S(O)^p$ and C(O);
Z is selected from:
  a $C_{3-13}$ carbocycle substituted with 0–5 $R^b$; and
  a 5–14 membered heterocycle comprising carbon atoms and 1–4 heteroatoms selected from the group consisting of N, O, and $S(O)_p$, and substituted with 0–5 $R^b$;
provided that Z is other than 2-oxo-1,4-pyridinylene;
$U^a$ is absent or is selected from: O, $NR^{a1}$, C(O), $CR^a(OH)$, C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_pNR^{a1}$, $NR^{a1}S(O)_p$, and $NR^{a1}SO_2NR^{a1}$;
$X^a$ is absent or is selected from $C_{1-10}$ alkylene, $C_{2-10}$ alkenylene, and $C_{2-10}$ alkynylene;
$Y^a$ is absent or is selected from O, $NR^{a1}$, $S(O)_p$, and C(O);
$Z^a$ is selected from H, a $C_{3-13}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;
provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;
$R^1$, at each occurrence, is independently selected from H, $CF_3$, $C_{1-6}$ alkyl substituted with 0–1 $R^b$, $C_{2-6}$ alkenyl substituted with 0–1 $R^b$, $C_{2-6}$ alkynyl substituted with 0–1 $R^b$, $(CR^aR^{a1})_sOR^{a1}$, $(CR^aR^{a1})_rNR^aR^{a1}$, $(CR^aR^{a1})_rC(O)$ $NR^aR^{a1}$, $(CR^aR^{a1})_r$—$C_{3-10}$ carbocycle substituted with 0–5 $R^d$, and $(CR^aR^{a1})_r$-5–10 membered heterocycle comprising carbon atoms and 1–4 heteroatoms selected from the group consisting of N, O, and $S(O)_p$, and substituted with 0–5 $R^d$;

$R^2$, at each occurrence, is independently selected from H, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$;

$R^3$, at each occurrence, is independently selected from H, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$;

$R^a$, at each occurrence, is independently selected from H, $C_{1-6}$ alkyl, phenyl, and benzyl;

$R^{a1}$, at each occurrence, is independently selected from H, $C_{1-6}$ alkyl substituted with 0–1 $R^e$, $C_{2-6}$ alkenyl substituted with 0–1 $R^e$, $C_{2-6}$ alkynyl substituted with 0–1 $R^e$, and —$(CH_2)_r$-3–8 membered carbocyclic or heterocyclic ring comprising carbon atoms and 0–2 ring heteroatoms selected from N, $NR^{a2}$, O, and $S(O)_p$ and substituted with 0–3 $R^e$;

alternatively, $R^a$ and $R^{a1}$, when attached to a nitrogen, are taken together with the nitrogen to which they are attached form a 5 or 6 membered heterocycle comprising carbon atoms and from 0–1 additional heteroatoms selected from N, $NR^{a2}$, O, and $S(O)_p$;

$R^{a2}$, at each occurrence, is independently selected from $C_{1-4}$ alkyl, phenyl, and benzyl;

$R^{a3}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —$(CH_2)_r$-3–8 membered carbocyclic or heterocyclic ring comprising carbon atoms and 0–2 ring heteroatoms selected from N, $NR^{a2}$, O, and $S(O)_p$, and substituted with 0–3 $R^{c1}$;

$R^b$, at each occurrence, is independently selected from $C_{1-6}$ alkyl substituted with 0–1 $R^{c1}$, $OR^a$, $SR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $NR^aC(O)NR^aR^{a1}$, $OC(O)NR^aR^{a1}$, $NR^aC(O)OR^a$, $S(O)_2NR^aR^{a1}$, $NR^aS(O)_2R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, $CF_2CF_3$, $CHF_2$, $CH_2F$, and phenyl;

$R^c$, at each occurrence, is independently selected from H, $OR^a$, Cl, F, Br, I, =O, —CN, $NO_2$, $CF_3$, $CF_2CF_3$, $OCF_3$, $(CR^aR^{a1})_rNR^aR^{a1}$, $(CR^aR^{a1})_rC(=NCN)NR^aR^{a1}$, $(CR^aR^{a1})_rC(=NR^a)NR^aR^{a1}$, $(CR^aR^{a1})_rC(=NOR^a)NR^aR^{a1}$, $(CR^aR^{a1})_rC(O)NR_aOH$, $(CR^aR^{a1})_rC(O)R^{a1}$, $(CR^aR^{a1})_rC(O)OR^{a1}$, $(CR^aR^{a1})_rC(S)OR^{a1}$, $(CR^aR^{a1})_rC(O)NR^aR^{a1}$, $(CR^aR^{a1})_rNR^aC(O)R^{a1}$, $(CR^aR^{a1})_rC(S)NR^aR^{a1}$, $(CR^aR^{a1})_rOC(O)NR^aR^{a1}$, $(CR^aR^{a1})_rNR^aC(O)OR^{a1}$, $(CR^aR^{a1})_rNR^aC(O)NR^aR^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$, $(CR^aR^{a1})_r NR^aSO_2NR^aR^{a1}$;

$C_{1-6}$ alkyl substituted with 0–2 $R^{c1}$;
$C_{2-6}$ alkenyl substituted with 0–2 $R^{c1}$;
$C_{2-6}$ alkynyl substituted with 0–2 $R^{c1}$;
$(CR^aR^{a1})_r$—$C_{3-10}$ carbocycle substituted with 0–2 $R^{c1}$; and
$(CR^aR^{a1})_r$-5–14 membered heterocycle comprising carbon atoms and 1–4 heteroatoms selected from the group consisting of N, O, and $S(O)_p$, and substituted with 0–2 $R^{c1}$;

alternatively, when two $R^c$ groups are attached to the same carbon atom, they form a spiro ring C that is a 3–11 membered carbocycle or heterocycle substituted with 0–2 $R^{c1}$ and comprising: carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

$R^{c1}$, at each occurrence, is independently selected from H, $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^{a1}$, $S(O)_2NR^aR^{a1}$, $NR^aS(O)_2 R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $OCF_3$, $CF_2CF_3$, $CH_2F$, and $CHF_2$;

$R^d$, at each occurrence, is independently selected from $C_{1-6}$ alkyl substituted with 0–2 $R^e$, $C_{2-6}$ alkenyl, $C_{2-6}$ alkynyl, $OR^a$, Cl, F, Br, I, =O, —CN, $NO_2$, $NR^aR^{a1}$, $C(O)R^{a1}$, $C(O)OR^a$, $C(O)NR^aR^{a1}$, $C(S)NR^aR^{a1}$, $R^aNC(O)NR^aR^{a1}$, $OC(O)NR^aR^{a1}$, $R^aNC(O)OR^{a1}$, $S(O)_2NR^aR^{a1}$, $NR^aS(O)_2 R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, and $CF_2CF_3$;

$R^e$, at each occurrence, is independently selected from H, $C_{1-6}$ alkyl, $OR^a$, Cl, F, Br, I, =O, —CN, $NO_2$, $NR^aR^a$, $C(O)R^a$, $C(O)OR^a$, $C(O)NR^aR^a$, $R^aNC(O)NR^aR^a$, $OC(O)NR^aR^a$, $R^aNC(O)OR^a$, $S(O)_2NR^aR^a$, $NR^aS(O)_2 R^{a2}$, $NR^aS(O)_2NR^aR^a$, $OS(O)_2NR^aR^a$, $NR^aS(O)_2R^{a2}$, $S(O)_pR^{a2}$, $CF_3$, $OCF_3$, $CF_2CF_3$, $CH_2F$, and $CHF_2$;

m, at each occurrence, is selected from 0, 1, 2 and 3;
p, at each occurrence, is selected from 0, 1, and 2;
r, at each occurrence, is selected from 0, 1, 2, 3, and 4;
s, at each occurrence, is selected from 1, 2, 3, and 4; and provided that
 i) when Z is phenylene or naphthylene, then $U^a$-$X^a$-$Y^a$-$Z^a$ forms a group other than H, $C_{1-6}$ alkyl, $NH_2$, $NHCOCH_3$, or naphthyl;
 ii) when W-U-X-Y forms —$NHSO_2$—, Z is naphthylene, then $Z^a$ is a group other than phenyl substituted with 0–5 $R^c$;
 iii) when W-U-X-Y forms —$NHSO_2$—, Z is phenylene, $U^a$-$X^a$-$Y^a$ forms a bond, then $Z^a$ is a group other than phenyl substituted with 0–5 $R^c$;
 iv) when W-U-X-Y forms —$NR^{a1}SO_2$—, Z is phenylene, then $Z^a$ is a group other than phenyl substituted with one 5–6 membered carbocycle or heterocycle substituted with 0–2 $R^{c1}$;
 v) when $R^1$ is $(CR^aR^{a1})_rNR^aR^{a1}$ or $(CR^aR^{a1})_rC(O)NR^aR^{a1}$, Z is phenylene or naphthylene, then $U^a$-$X^a$-$Y^a$ forms a group other than a bond and $Z^a$ is other than H; and
 vi) when W-U-X-Y forms —$NHSO_2CH_2$— or —$NHCOCH_2$—, Z is naphthyl, then $U^a$-$X^a$-$Y^a$ forms other than $CH_2CH_2NR^{1a}$.

[2] In another embodiment, the present invention provides a novel compound of formula I, wherein;

W is $(CHR^a)_m$;
U is absent or is selected from: $CR^a(OH)$, $C(O)O$, $OC(O)$, $C(O)NR^{a1}$, $NR^{a1}C(O)$, $OC(O)NR^{a1}$, $NR^{a1}C(O)O$, $NR^{a1}C(O)NR^{a1}$, $OS(O)_2$, $S(O)_2O$, $S(O)_2$, $S(O)_pNR^{a1}$, $NR^{a1}S(O)_p$, and $NR^{a1}SO_2NR^{a1}$;
X is absent or is $C_{1-3}$ alkylene;
Y is absent;
$U^a$ is absent or is selected from: O, $NR^{a1}$, C(O), $CR^a(OH)$, C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{3-13}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, $C_{2-6}$ alkynyl substituted with 0–1 $R^b$, $(CR^aR^{a1})_sOR^{a1}$, $(CR^aR^{a1})_rNR^aR^{a1}$, $(CR^aR^{a1})_rC(O)NR^aR^{a1}$, $(CR^aR^{a1})_r$—$C_{3-10}$ carbocycle substituted with 0–3 $R^d$, and $(CR^aR^{a1})_r$-5–10 membered heterocycle comprising carbon atoms and 1–4 heteroatoms selected from the group consisting of N, O, and $S(O)_p$, and substituted with 0–3 $R^d$;

$R^2$, at each occurrence, is independently selected from H, $C_{1-6}$ alkyl, $C_{2-6}$ alkenyl, and $C_{2-6}$ alkynyl;

$R^3$, at each occurrence, is independently selected from H, $C_{1-6}$ alkyl, $C_{2-6}$ alkenyl, and $C_{2-6}$ alkynyl;

$R^a$, at each occurrence, is independently selected from H, $C_{1-6}$ alkyl, phenyl, and benzyl;

$R^{a1}$, at each occurrence, is independently selected from H, $C_{1-6}$ alkyl, phenyl, and benzyl;

$R^{a3}$, at each occurrence, is independently selected from H, $C_{1-4}$ alkyl, phenyl, and benzyl; and $R^c$, at each occurrence, is independently selected from H, $OR^a$, Cl, F, Br, $=$O, —CN, $NO_2$, $NR^aR^{a1}$, $CF_3$, $(CR^aR^{a1})_r$ $C(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and $(CH_2)_r$-5–6 membered heterocycle comprising carbon atoms and 1–4 heteroatoms selected from the group consisting of N, O, and $S(O)_p$, and substituted with 0–2 $R^{c1}$.

[3] In another embodiment, the present invention provides a novel compound of formula I, wherein;

W is absent or is $CH_2$;

U is selected from: C(O)NH, NHC(O), $OS(O)_2$, $S(O)_2O$, $S(O)_2$, $S(O)_2NH$, and $NHS(O)_2$;

X is absent;

Y is absent;

Z is selected from:
  phenylene substituted with 0–5 $R^b$;
  naphthylene substituted with 0–5 $R^b$; and
  a 5–14 membered heterocycle comprising carbon atoms and 1–4 heteroatoms selected from the group consisting of N, O, and $S(O)_p$, and substituted with 0–5 $R^b$;

$U^a$ is absent or is selected from: O, $NR^{a1}$, and $CR^a(OH)$;

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{5-10}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_sOR^{a1}$, and $(CH_2)_rNR^aR^{a1}$;

$R^2$, at each occurrence, is independently selected from H and $C_{1-4}$ alkyl;

$R^3$, at each occurrence, is independently selected from H and $C_{1-4}$ alkyl;

$R^a$, at each occurrence, is independently selected from H and $C_{1-6}$ alkyl;

$R^{a1}$, at each occurrence, is independently selected from H and $C_{1-6}$ alkyl;

$R^{a3}$, at each occurrence, is independently selected from H, $C_{1-4}$ alkyl, phenyl, and benzyl; and $R^c$, at each occurrence, is independently selected from H, $OR^a$, Cl, F, Br, $=$O, —CN, $NO_2$, $NR^aR^{a1}$, $CF_3$, $(CR^aR^{a1})_r$ $C(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and $(CH_2)_r$-5–6 membered heterocycle comprising carbon atoms and 1–4 heteroatoms selected from the group consisting of N, O, and $S(O)_p$, and substituted with 0–2 $R^{c1}$.

[4] In another embodiment, the present invention provides a novel compound of formula I, wherein;

W is absent or is $CH_2$;

U is selected from: NHC(O), $OS(O)_2$, $S(O)_2$, and $NHS(O)_2$;

X is absent;

Y is absent;

Z is selected from:
  phenylene substituted with 0–5 $R^b$; and
  naphthylene substituted with 0–5 $R^b$;

$U^a$ is absent or is 0;

$X^a$ is absent or is $CH_2$ or $CH_2CH_2$;

$Y^a$ is absent or is 0;

$Z^a$ is a 5–10 membered heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolyl;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_sOR^{a1}$, and $(CH_2)_rNR^aR^{a1}$; and $R^c$, at each occurrence, is independently selected from H, $OR^a$, Cl, F, Br, $=$O, —CN, $NO_2$, $NR^aR^{a1}$, $CF_3$, $(CH_2)_rC(O)R^{a1}$, $(CH_2)_rC(O)OR^{a1}$, $(CH_2)_rC(O)NR^aR^{a1}$, $(CH_2)_rNR^aC(O)R^{a1}$, $(CH_2)_rS(O)_pR^{a3}$, $(CH_2)_rSO_2NR^aR^{a1}$, $(CH_2)_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and (CH₂)ᵣ-5–6 membered heterocycle comprising carbon atoms and 1–4 heteroatoms selected from the group consisting of N, O, and S(O)ₚ, and substituted with 0–2 R^{c1}.

[5] In another embodiment, the present invention provides a novel compound of formula Ia:

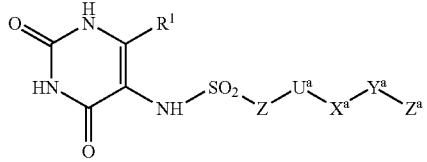

or a stereoisomer or pharmaceutically acceptable salt form thereof, wherein;

Z is selected from:
a C₃₋₁₃ carbocycle substituted with 0–5 R^b; and
a 5–14 membered heterocycle comprising carbon atoms and 1–4 heteroatoms selected from the group consisting of N, O, and S(O)ₚ, and substituted with 0–5 R^b;
provided that Z is other than 2-oxo-1,4-pyridinylene;

U^a is absent or is selected from: O, NR^{a1}, C(O), CR^a(OH), C(O)O, OC(O), C(O)NR^{a1}, NR^{a1}C(O), OC(O)O, OC(O)NR^{a1}, NR^{a1}C(O)O, NR^{a1}C(O)NR^{a1}, S(O)ₚ, S(O)ₚNR^{a1}, NR^{a1}S(O)ₚ, and NR^{a1}SO₂NR^{a1};

X^a is absent or is selected from C₁₋₁₀ alkylene, C₂₋₁₀ alkenylene, and C₂₋₁₀ alkynylene;

Y^a is absent or is selected from O, NR^{a1}, S(O)ₚ, and C(O);

Z^a is selected from H, a C₃₋₁₃ carbocycle substituted with 0–5 R^c, and a 5–14 membered heterocycle comprising carbon atoms and 1–4 heteroatoms selected from the group consisting of N, O, and S(O)ₚ, and substituted with 0–5 R^c;

provided that U, Y, Z, U^a, Y^a, and Z^a do not combine to form a N—N, N—O, O—N, O—O, S(O)ₚ—O, O—S(O)ₚ or S(O)ₚ—S(O)ₚ group;

R¹, at each occurrence, is independently selected from H, CF₃, C₁₋₆ alkyl substituted with 0–1 R^b, C₂₋₆ alkenyl substituted with 0–1 R^b, C₂₋₆ alkynyl substituted with 0–1 R^b, (CR^aR^{a1})ₛOR^{a1}, (CR^aR^{a1})ᵣNR^aR^{a1}, (CR^aR^{a1})ᵣC(O)NR^aR^{a1}, (CR^aR^{a1})ᵣ—C₃₋₁₀ carbocycle substituted with 0–5 R^d, and (CR^aR^{a1})ᵣ-5–10 membered heterocycle comprising carbon atoms and 1–4 heteroatoms selected from the group consisting of N, O, and S(O)ₚ, and substituted with 0–5 R^d;

R^a, at each occurrence, is independently selected from H, C₁₋₆ alkyl; phenyl, and benzyl;

R^{a1}, at each occurrence, is independently selected from H, C₁₋₆ alkyl substituted with 0–1 R^e, C₂₋₆ alkenyl substituted with 0–1 R^e, C₂₋₆ alkynyl substituted with 0–1 R^e, and —(CH₂)ᵣ-3–8 membered carbocyclic or heterocyclic ring comprising carbon atoms and 0–2 ring heteroatoms selected from N, NR^{a2}, O, and S(O)ₚ, and substituted with 0–3 R^e;

alternatively, R^a and R^{a1}, when attached to a nitrogen, are taken together with the nitrogen to which they are attached form a 5 or 6 membered heterocycle comprising carbon atoms and from 0–1 additional heteroatoms selected from N, NR^{a2}, O, and S(O)ₚ;

R^{a2}, at each occurrence, is independently selected from C₁₋₄ alkyl, phenyl, and benzyl;

R^{a3}, at each occurrence, is independently selected from H, C₁₋₆ alkyl substituted with 0–1 R^{c1}, C₂₋₆ alkenyl substituted with 0–1 R^{c1}, C₂₋₆ alkynyl substituted with 0–1 R^{c1}, and —(CH₂)ᵣ-3–8 membered carbocyclic or heterocyclic ring comprising carbon atoms and 0–2 ring heteroatoms selected from N, NR^{a2}, O, and s(O)ₚ, and substituted with 0–3 R^{c1};

R^b, at each occurrence, is independently selected from C₁₋₆ alkyl substituted with 0–1 R^{c1}, OR^a, SR^a, Cl, F, Br, I, =O, —CN, NO₂, NR^aR^{a1}, C(O)R^a, C(O)OR^a, C(O)NR^aR^{a1}, C(S)NR^aR^{a1}, NR^aC(O)NR^aR^{a1}, OC(O)NR^aR^{a1}, NR^aC(O)OR^a, S(O)₂NR^aR^{a1}, NR^aS(O)₂R^{a3}, NR^aS(O)₂NR^aR^{a1}, OS(O)₂NR^aR^{a1}, NR^aS(O)₂R^{a3}, S(O)ₚR^{a3}, CF₃, CF₂CF₃, CHF₂, CH₂F, and phenyl;

R^c, at each occurrence, is independently selected from H, OR^a, Cl, F, Br, I, =O, —CN, NO₂, CF₃, CF₂CF₃, CH₂F, CHF₂, CF₂CH₃, C(CH₃)₂F, OCF₃, (CR^aR^{a1})ᵣNR^aR^{a1}, (CR^aR^{a1})ᵣC(=NCN)NR^aR^{a1}, (CR^aR^{a1})ᵣC(=NR^a)NR^aR^{a1}, (CR^aR^{a1})ᵣC(=NOR^a)NR^aR^{a1}, (CR^aR^{a1})ᵣC(O)NR^aOH, (CR^aR^{a1})ᵣC(O)R^{a1}, (CR^aR^{a1})ᵣC(O)OR^{a1}, (CR^aR^{a1})ᵣC(S)OR^{a1}, (CR^aR^{a1})ᵣC(O)NR^aR^{a1}, (CR^aR^{a1})ᵣNR^aC(O)R^{a1}, (CR^aR^{a1})ᵣC(S)NR^aR^{a1}, (CR^aR^{a1})ᵣOC(O)NR^aR^{a1}, (CR^aR^{a1})ᵣNR^aC(O)OR^{a1}, (CR^aR^{a1})ᵣNR^aC(O)NR^aR^{a1}, (CR^aR^{a1})ₛS(O)ₚR^{a3}, (CR^aR^{a1})ₛSO₂NR^aR^{a1}, (CR^aR^{a1})ᵣNR^aSO₂R^{a3}, (CR^aR^{a1})ᵣNR^aSO₂NR^aR^{a1};
C₁₋₆ alkyl substituted with 0–2 R^{c1};
C₂₋₆ alkenyl substituted with 0–2 R^{c1};
C₂₋₆ alkynyl substituted with 0–2 R^{c1};
(CR^aR^{a1})ᵣ—C₃₋₁₀ carbocycle substituted with 0–2 R^{c1}; and
(CR^aR^{a1})ᵣ-5–14 membered heterocycle comprising carbon atoms and 1–4 heteroatoms selected from the group consisting of N, O, and S(O)ₚ, and substituted with 0–2 R^{c1};

alternatively, when two R^c groups are attached to the same carbon atom, they form a spiro ring C that is a 3–11 membered carbocycle or heterocycle substituted with 0–2 R^{c1} and comprising: carbon atoms, 0–4 ring heteroatoms selected from O, N, and S(O)ₚ, and 0–2 double bonds, provided that ring C contains other than a S—S, O—O, or S—O bond;

alternatively, when two R^c groups are attached to adjacent carbon atoms, together with the carbon atoms to which they are attached they form a 5–7 membered carbocyclic or heterocyclic ring D substituted with 0–2 R^{c1} and consisting of carbon atoms, 0–2 heteroatoms selected from the group consisting of N, O, and S(O)ₚ, and 0–3 double bonds;

R^{c1}, at each occurrence, is independently selected from H, C₁₋₆ alkyl, OR^a, Cl, F, Br, I, =O, —CN, NO₂, NR^aR^{a1}, C(O)R^a, C(O)OR^a, C(O)NR^aR^{a1}, R^aNC(O)NR^aR^{a1}, OC(O)NR^aR^{a1}, R^aNC(O)OR^{a1}, S(O)₂NR^aR^{a1}, NR^aS(O)₂R^{a2}, NR^aS(O)₂NR^aR^{a1}, OS(O)₂NR^aR^{a1}, NR^aS(O)₂R^{a2}, S(O)ₚR^{a2}, CF₃, OCF₃, CF₂CF₃, CH₂F, and CHF₂;

R^d, at each occurrence, is independently selected from C₁₋₆ alkyl substituted with 0–2 R^e, C₂₋₆ alkenyl, C₂₋₆ alkynyl, OR^a, Cl, F, Br, I, =O, —CN, NO₂, NR^aR^{a1}, C(O)R^a, C(O)OR^a, C(O)NR^aR^{a1}, C(S)NR^aR^{a1}, R^aNC(O)NR^aR^{a1}, OC(O)NR^aR^{a1}, R^aNC(O)OR^{a1}, S(O)₂NR^aR^{a1}, NR^aS(O)₂R^{a3}, NR^aS(O)₂NR^aR^{a1}, OS(O)₂NR^aR^{a1}, NR^aS(O)₂R^{a3}, S(O)ₚR^{a3}, CF₃, and CF₂CF₃;

R^e, at each occurrence, is independently selected from H, C₁₋₆ alkyl, OR^a, Cl, F, Br, I, =O, —CN, NO₂, NR^aR^a, C(O)R^a, C(O)OR^a, C(O)NR^aR^a, R^aNC(O)NR^aR^a, OC(O)NR^aR^a, R^aNC(O)OR^a, S(O)₂NR^aR^a, NR^aS(O)₂R^{a2}, NR^aS(O)₂NR^aR^a, OS(O)₂NR^aR^a, NR^aS(O)₂R^{a2}, S(O)ₚR^{a2}, CF₃, OCF₃, CF₂CF₃, CH₂F, and CHF₂;

p, at each occurrence, is selected from 0, 1, and 2;

r, at each occurrence, is selected from 0, 1, 2, 3, and 4;

s, at each occurrence, is selected from 1, 2, 3, and 4; and provided that
   i) when Z is phenylene or naphthylene, then $U^a$-$X^a$-$Y^a$-$Z^a$ forms a group other than H, $C_{1-6}$ alkyl, $NH_2$, $NHCOCH_3$, or naphthyl;
   ii) when Z is naphthylene, then $Z^a$ is a group other than phenyl substituted with 0–5 $R^c$;
   iii) when Z is phenylene, $U^a$-$X^a$-$Y^a$ forms a bond, then $Z^a$ is a group other than phenyl substituted with 0–5 $R^c$;
   iv) when Z is phenylene, then $Z^a$ is a group other than phenyl substituted with one 5–6 membered carbocycle or heterocycle substituted with 0–2 $R^{c1}$; and
   v) when $R^1$ is $(CR^aR^{a1})_rNR^aR^{a1}$ or $(CR^aR^{a1})_rC(O)NR^aR^{a1}$, Z is phenylene or naphthylene, then $U^a$-$X^a$-$Y^a$ forms a group other than a bond and $Z^a$ is other than H.

[6] In another embodiment, the present invention provides a novel compound of formula Ia, wherein;

$U^a$ is absent or is selected from: O, $NR^{a1}$, and $CR^a(OH)$;

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{3-13}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, $C_{2-6}$ alkynyl substituted with 0–1 $R^b$, $(CR^aR^{a1})$ $OR^{a1}$, $(CR^aR^{a1})_rNR^aR^{a1}$, $(CR^aR^{a1})_rC(O)NR^aR^{a1}$, $(CR^aR^{a1})_r$—$C_{3-10}$ carbocycle substituted with 0–3 $R^d$, and $(CR^aR^{a1})_r$-5–10 membered heterocycle comprising carbon atoms and 1–4 heteroatoms selected from the group consisting of N, O, and $S(O)_p$, and substituted with 0–3 $R^d$;

$R^a$, at each occurrence, is independently selected from H, $C_{1-6}$ alkyl, phenyl, and benzyl;

$R^{a1}$, at each occurrence, is independently selected from H, $C_{1-6}$ alkyl, phenyl, and benzyl;

$R^{a3}$, at each occurrence, is independently selected from H, $C_{1-4}$ alkyl, phenyl, and benzyl;

$R^c$, at each occurrence, is independently selected from H, $OR^a$, Cl, F, Br, =O, —CN, $NO_2$, $NR^aR^{a1}$, $CF_3$, $(CR^aR^{a1})_r$ $C(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_r$ $SO_2NR^aR^{a1}$, $(CR^aR^{a1})_rNR^aSO_2R^{a3}$; and
$C_{1-6}$ alkyl substituted with 0–1 $R^{c1}$;
$C_{2-6}$ alkenyl substituted with 0–1 $R^{c1}$;
$C_{2-6}$ alkynyl substituted with 0–1 $R^{c1}$;
$(CH_2)_r$—$C_{3-6}$ carbocycle substituted with 0–2 $R^{c1}$; and
$(CH_2)_r$-5–6 membered heterocycle comprising carbon atoms and 1–4 heteroatoms selected from the group consisting of N, O, and $S(O)_p$, and substituted with 0–2 $R^{c1}$.

[7] In another embodiment, the present invention provides a novel compound of formula Ia, wherein;

Z is selected from:
   phenylene substituted with 0–5 $R^b$;
   naphthylene substituted with 0–5 $R^b$; and
   a 5–14 membered heterocycle comprising carbon atoms and 1–4 heteroatoms selected from the group consisting of N, O, and $S(O)_p$, and substituted with 0–5 $R^b$;

$U^a$ is absent or is selected from: O, $NR^{a1}$, and $CR^a(OH)$;

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{5-10}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_sOR^{a1}$, and $(CH_2)_rNR^aR^{a1}$;

$R^a$, at each occurrence, is independently selected from H and $C_{1-6}$ alkyl;

$R^{a1}$, at each occurrence, is independently selected from H and $C_{1-6}$ alkyl;

$R^{a3}$, at each occurrence, is independently selected from H, $C_{1-4}$ alkyl, phenyl, and benzyl; and $R^c$, at each occurrence, is independently selected from H, $OR^a$, Cl, F, Br, =O, —CN, $NO_2$, $NR^aR^{a1}$, $CF_3$, $(CR^aR^{a1})_r$ $C(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_r$ $SO_2NR^aR^{a1}$, $(CR^aR^{a1})_rNR^aSO_2R^{a3}$;
$C_{1-6}$ alkyl substituted with 0–1 $R^{c1}$;
$C_{2-6}$ alkenyl substituted with 0–1 $R^{c1}$;
$C_{2-6}$ alkynyl substituted with 0–1 $R^{c1}$;
$(CH_2)_r$—$C_{3-6}$ carbocycle substituted with 0–2 $R^{c1}$; and
$(CH_2)_r$-5–6 membered heterocycle comprising carbon atoms and 1–4 heteroatoms selected from the group consisting of N, O, and $S(O)_p$, and substituted with 0–2 $R^{c1}$.

[8] In another embodiment, the present invention provides a novel compound of formula Ia, wherein;

Z is selected from:
   phenylene substituted with 0–3 $R^b$; and
   naphthylene substituted with 0–3 $R^b$;

$U^a$ is absent or is O;

$X^a$ is absent or is $CH_2$ or $CH_2CH_2$;

$Y^a$ is absent or is O;

$Z^a$ is a 5–10 membered heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolyl;

provided that $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_sOR^{a1}$, and $(CH_2)_rNR^aR^{a1}$; and $R^c$, at each occurrence, is independently selected from H, $OR^a$, Cl, F, Br, =O, —CN, $NO_2$, $NR^aR^{a1}$, $CF_3$, $(CH_2)_r$ $C(O)R^{a1}$, $(CH_2)_rC(O)OR^{a1}$, $(CH_2)_rC(O)NR^aR^{a1}$, $(CH_2)_r$ $NR^aC(O)R^{a1}$, $(CH_2)_rS(O)_pR^{a3}$, $(CH_2)_rSO_2NR^aR^{a1}$, $(CH_2)_rNR^aSO_2R^{a3}$;
$C_{1-6}$ alkyl substituted with 0–1 $R^{c1}$;
$C_{2-6}$ alkenyl substituted with 0–1 $R^{c1}$;
$C_{2-6}$ alkynyl substituted with 0–1 $R^{c1}$;
$(CH_2)_r$—$C_{3-6}$ carbocycle substituted with 0–2 $R^{c1}$; and (CH$_2$)$_r$-5–6 membered heterocycle comprising carbon atoms and 1–4 heteroatoms selected from the group consisting of N, O, and S(O)$_p$ and substituted with 0–2 R$^{c1}$.

[9] In another preferred embodiment, the present invention provides a novel compound selected from the group:

N-(2,4-dioxo-1,2,3,4-tetrahydro-5-pyrimidinyl)-4-[(2-methyl-4-quinolinyl)methoxy]benzenesulfonamide;

N-(2,4-dioxo-1,2,3,4-tetrahydro-5-pyrimidinyl)-6-[(2-methyl-4-quinolinyl)methoxy]-2-naphthalenesulfonamide;

N-(6-amino-2,4-dioxo-1,2,3,4-tetrahydro-5-pyrimidinyl)-4-[(2-methyl-4-quinolinyl)methoxy]benzenesulfonamide;

2,4-dioxo-1,2,3,4-tetrahydro-5-pyrimidinyl 4-[(2-methyl-4-quinolinyl)methoxy]benzenesulfonate;

N-(2,4-dioxo-1,2,3,4-tetrahydro-5-pyrimidinyl)-4-[(2-methyl-4-quinolinyl)methoxy]benzamide;

N-(2,4-dioxohexahydro-5-pyrimidinyl)-4-[(2-methyl-4-quinolinyl)methoxy]benzenesulfonamide;

N-(2,4-dioxohexahydro-5-pyrimidinyl)-4-[(2-methyl-4-quinolinyl)methoxy]benzamide;

N-[(2,4-dioxo-1,2,3,4-tetrahydro-5-pyrimidinyl)methyl]-4-[(2-methyl-4-quinolinyl)methoxy]benzenesulfonamide;

6-({4-[(2-methyl-4-quinolinyl)methoxy]phenyl}thio)-2,4(1H,3H)-pyrimidinedione;

N-(2,4-dioxo-1,2,3,4-tetrahydro-5-pyrimidinyl)-4-phenoxybenzenesulfonamide;

or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt form thereof.

In another embodiment, the present invention provides a novel method comprising: administering a compound of the present invention or a pharmaceutically acceptable salt form thereof in an amount effective to treat a condition or disease mediated by MMPs, TACE, aggrecanase, or a combination thereof.

In another embodiment, the present invention provides a novel method of treating a disease or condition, wherein the disease or condition is selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, aggrecanase, or a combination thereof.

In another embodiment, the present invention provides a method for treating inflammatory disorders, comprising: administering, to a mammal in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

In another embodiment, the present invention provides a medical device for implanting into a mammalian body wherein the medical device has a coating material comprising an amount of one of the compounds of the present invention or a pharmaceutically-acceptable salt, hydrate, or prodrug thereof, effective for reducing inflammation or restinosis.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, and racemic forms and all geometric isomeric forms of a structure are intended, unless the specific stereochemistry or isomeric form is specifically indicated. All processes used to prepare compounds of the present invention and intermediates made therein are considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "independently selected from", "independently, at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with MCPBA and or hydrogen peroxides to afford other compounds of this invention. Thus, all shown amines are considered to cover both the shown amine and its N-oxide (N→O) derivative.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, and 3,4-dihydro-2H-chromen-4-yl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a mammal. The combination of compounds is preferably a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anti-inflammatory effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The compound of this invention like formula Ia where in $U^a$ is O, may be prepared by methods described in Scheme 1. The 4-hydroxybenzene sulfonic acid sodium salt is combined with an appropriately substituted alkyl halide, or mesylate in a solvent like methanol and a base like sodium methoxide at elevated temperatures. The compound of formula 2 is reacted with thionyl chloride, oxalyl or phosphorous trichloride in an appropriate solvent to make the sulfonyl chloride compound formula 3. The sulfonyl chloride is reacted with an amine like 5-amino uracil or 5-amino dihydrouracil in pyridine or dioxane with aqueous sodium bicarbonate to give the target molecule compound of formula 4.

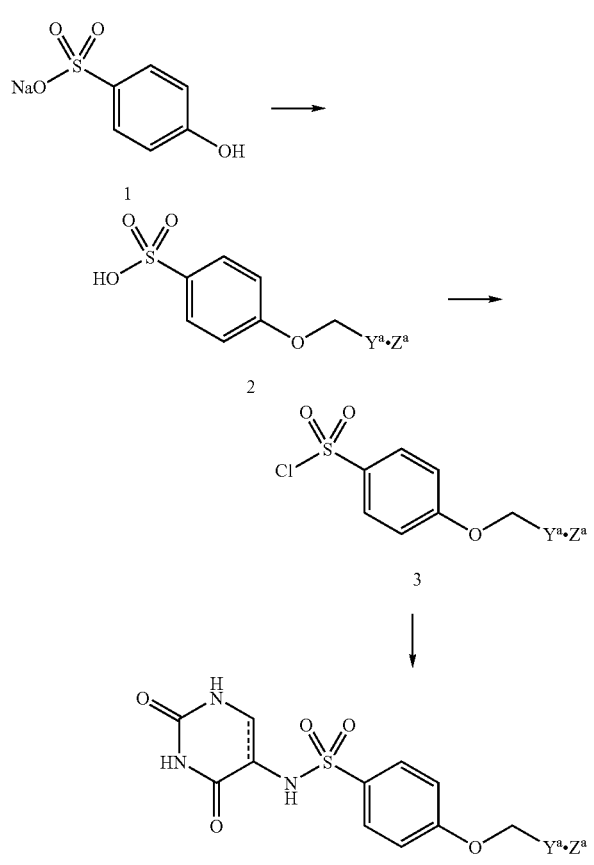

Alternatively, 2-amino malonate, or 2-amino acetoacetate can be reacted with compound of formula 3 in pyridine or methylene chloride with aqueous carbonate to give an intermediate like compound of formula 5. The final compounds of formula 6-may be prepared by treating compounds of formula 5 with urea or thiourea in a solvent like ethanol at elevated temperatures.

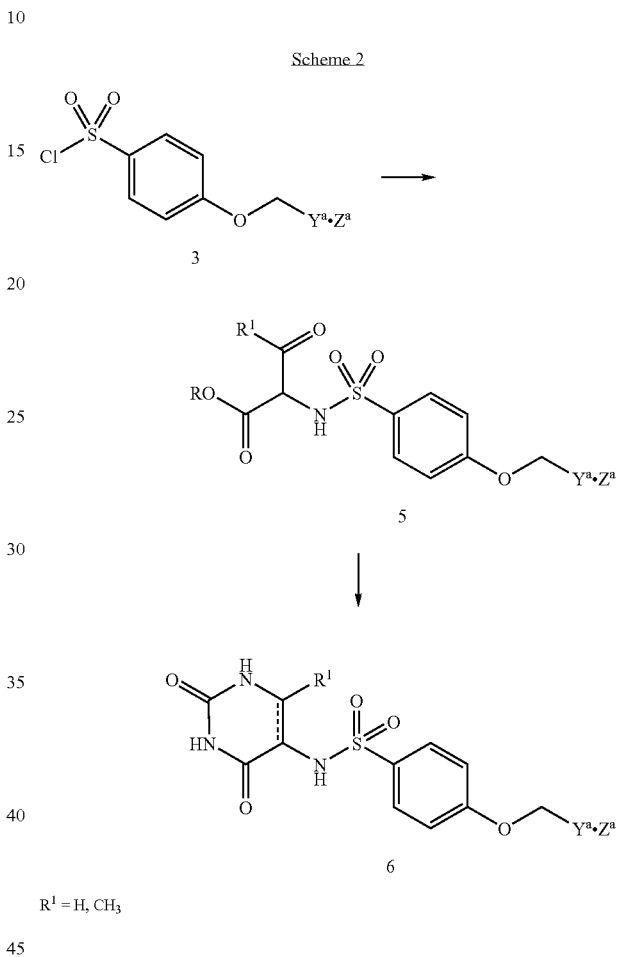

$R^1$ = H, CH$_3$

The compound of this invention of formula I wherein A is $A_1$, U is —NHC(=O)—, may be prepared by methods described in Scheme 3. Methyl 4-hydroxybenzoate can be alkylated with an appropriately substituted alkyl bromide, mesylate or similar leaving group, in acetonitrile, acetone or DMSO with a base like cesium carbonate or sodium carbonate at room temperature or elevated temperatures up to reflux of the solvent. The compound of formula 7, is saponified with lithium hydroxide in methanol or THF or combinations of similar solvents and water to give the carboxylic acid compound of formula 8. The acid chloride compound of formula 9 can be prepared by treating the acid of formula 8 with thionyl chloride neat or in combination with solvents similar to methylene chloride and elevated temperatures. The compounds of formula I wherein A is A1, U is —NHC(=O)— are prepared by treating the 5-amino uracil with the acid chloride compound of formula 9 in pyridine or dioxane with aqueous carbonate at room temperature.

Scheme 3

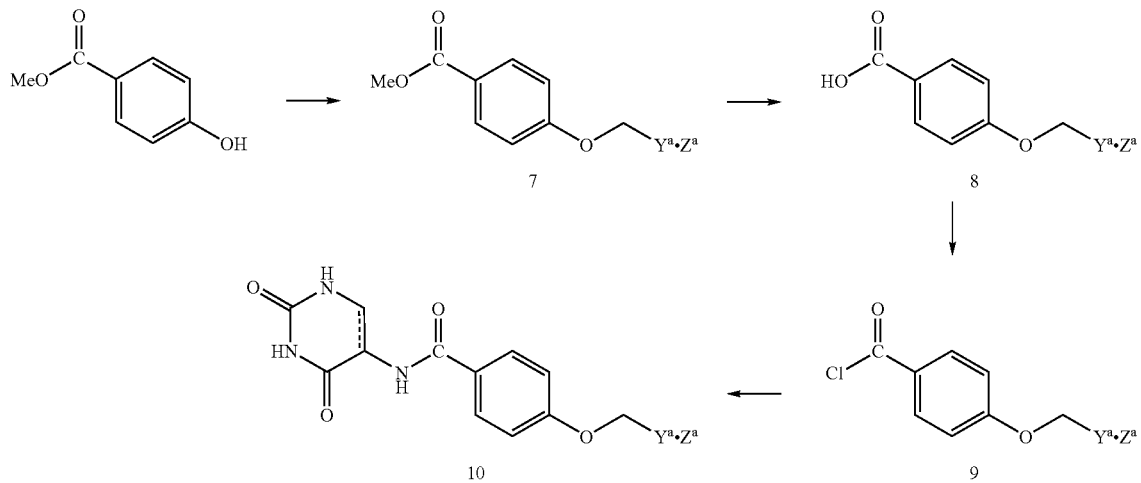

The compound of this invention of formula I wherein A is $A_2$, W is methylene and U is —S(=O)$_2$—, may be prepared by methods described in scheme 4. (6-chloromethyl)uracil is treated with 4-mercaptophenol in DMSO and a base like cesium carbonate, to give the compound of formula 11. The compound of formula 12 may be prepared by treating the phenol compound of formula 11 with an appropriately substituted alkyl halide or mesylate in a solvent such as acetone or DMSO with a base like cesium carbonate. The sulfone compound of formula 13 may be prepared by treating the sulphide compound of formula 12 with Oxone® in mixtures of THF and water.

Scheme 4

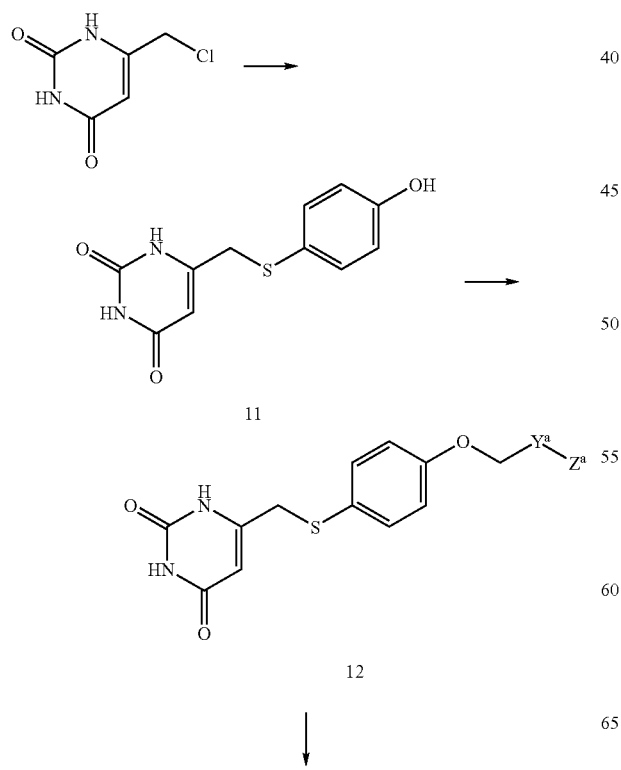

-continued

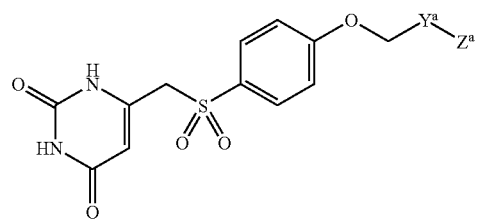

The compound of this invention of formula I wherein A is $A_1$, W is methylene and U is —NHS(=O)$_2$— or —NHC(=O)— may be prepared by methods described in scheme 5. The (5-hydroxymethyl)uracil compound of formula 14 was prepared by methods known in the literature (Cline, R. E. et al. *J. Am. Chem. Soc.* 1959, 81, 2521). The (5-choromethyl)uracil was prepared by treating the (5-hydroxymethyl) uracil compound of formula 14 with thionyl chloride in dioxane at reflux. The (5-aminomethyl)uracil was prepared by treating the (5-chloromethyl)uracil compound of formula 15 with sodium azide in DMSO and then reducing the intermediate azide with hydrogen and palladium on carbon in mixtures of ethanol:water as solvent, alternatively other methods well known in the literature for reducing azide may be used. The (5-aminomethyl)uracil compound of formula 17 was treated with an appropriately substituted sulfonyl chloride like compound of formula 4 or the acid chloride compound of formula 9, as previously described.

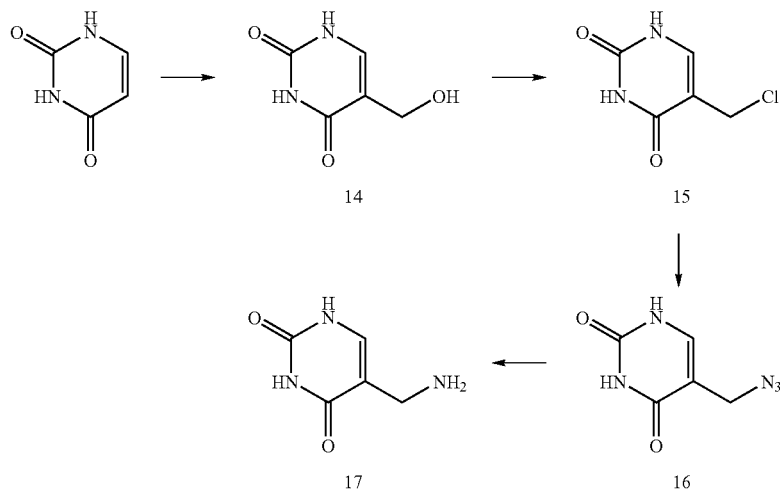

The compound of this invention of formula I wherein A is $A_1$, W is absent and U is —S(=O)$_2$NH— may be prepared by methods described in scheme 6. The (5-sulfonyl chloride) uracil compound of formula 18 was prepared by treating uracil with chlorosulfonic acid at reflux (Herr, R. R. et al. *J. Am. Chem. Soc.* 1956, 78, 401). The sulfonamide compound of formula 19 was prepared by treating the (5-sulfonyl chloride)uracil compound of formula 18 with an appropriately substituted amine in dioxane and aqueous bicarbonate or pyridine.

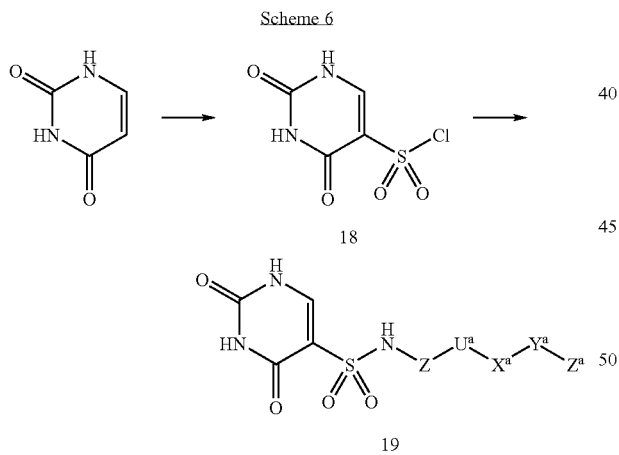

The compound of this invention like formula I wherein A is $A_1$, W is absent and U is —NHS(=O)$_2$NH— may be prepared by methods described in scheme 7. The sulfonylcarbamate compound of formula 21 was prepared by treating the 5-aminouracil with the catcholsulfonate compound of formula 20 (G. E. DuBois and R. A. Stephson, *J. Org. Chem.* 1980, 45, 5371–5373; G. DuBois, *J. Org. Chem.* 1980, 45, 5373–5375) in DMSO with DBU. The intermediate sulfonylcarbamate compound of formula 21 was treated with an appropriately substituted amine in DMSO at elevated temperatures to give the sulfonyl urea compounds of formula 22.

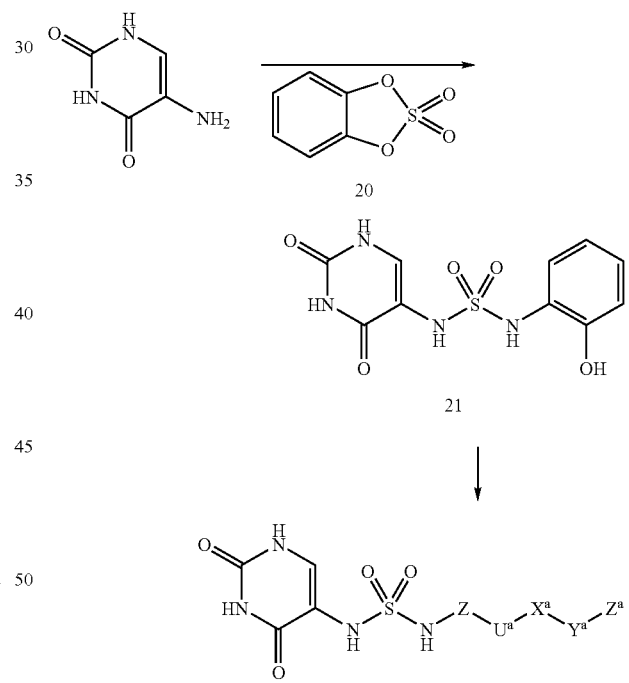

Alternatively the compound of this invention of formula I wherein A is $A_1$, W is absent and U is —NHS(=O)$_2$NH— may be prepared by methods described in scheme 8. The appropriately substituted amine maybe reacted with the catcholsulfonate compound of formula 20 in solvents like DMSO or ethanol to give the sulfonylcarbamte compound of formula 23. Then the intermediate carbamate compound 23 was reacted with the appropriate amino uracil to give the target compound 22.

Scheme 8

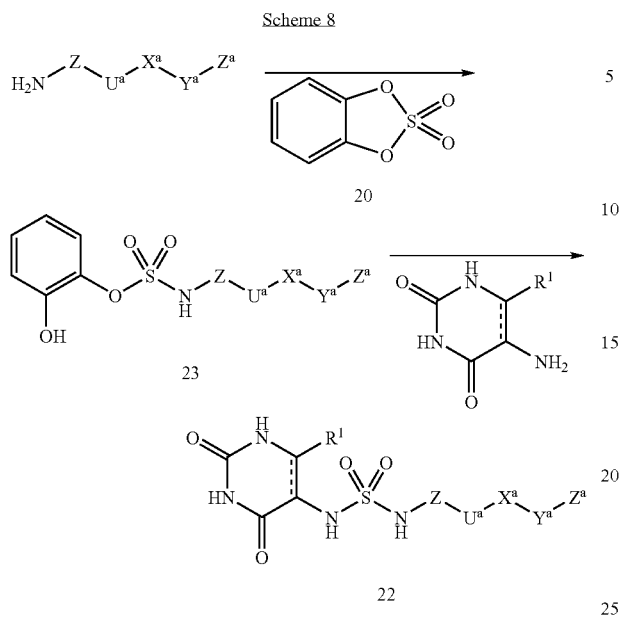

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 2

N-(2,4-dioxo-1,2,3,4-tetrahydro-5-pyrimidinyl)-4-[(2-methyl-4-quinolinyl)methoxy]benzenesulfonamide trifluoroacetate (2a) Sodium hydroxide 3.0 M (8.7 ml) was added to a suspension of 4-hydroxybezenesulfonic acid sodium salt (5.0 g, 22.0 mmol), 4-chloromethyl-2-methylquinoline (5.0 g, 26.0 mmol) and sodium iodide (0.4 g, 2.7 mmol) in ethanol (80 ml). The reaction was heated to reflux for 18 h, allowed to cool to room temperature to crystallize a white solid. The solids were filtered off, washed with ethanol, chloroform and dried in vacuo to give 4-[(2-methyl-4-quinolinyl)methoxy]benzenesulfonic acid sodium salt (5.5 g, 73%) as a crystalline solid. MS found: (M−Na)$^−$=328.

(2b) A catalytic amount of DMF was added to a solution of the 4-[(2-methyl-4-quinolinyl)methoxy]benzenesulfonic acid sodium salt (1.0 g, 2.8 mmol) from step (2a) in thionyl chloride (3.0 ml, 41.0 mmol). The reaction was heated to 60° C. for 2 h, allowed to cool to room temperature, diluted with methylene chloride, concentrated in vacuo, diluted with THF, concentrated in vacuo to give 4-[(2-methyl-4-quinolinyl)methoxy]benzenesulfonyl chloride (0.95 g, 97%) as a light yellow solid.

(2c) 4-[(2-methyl-4-quinolinyl)methoxy]benzenesulfonyl chloride from step 2b (0.23 g, 1.18 mmol) was added to a solution of 5-amino uracil (0.15 g, 1.18 mmol) in pyridine (5 ml) under nitrogen atmosphere at room temperature. The reaction was stirred for 2.5 h, was concentrated in vacuo to give a solid residue. The product was prepared and purified by HPLC on a C-18 column eluting with an acetonitrile: water: TFA gradient to give the title compound (0.075 g, 60%) as a white amorphous solid. MS found: (M+H)$^+$=439.

Example 3

N-(2,4-dioxo-1,2,3,4-tetrahydro-5-pyrimidinyl)-6-[(2-methyl-4-quinolinyl)methoxy]-2-naphthalenesulfonamide trifluoroacetate Following a procedure analogous to that used in Example 2, but using 2-napthol-6-sulfonic acid sodium salt in step (2a), the product was prepared and purified by HPLC on a C-18 column eluting with an acetonitrile: water: TFA gradient to give the title compound (0.042 g, 16%) as a white amorphous solid. MS found: (M+H)$^+$=489.

Example 4

N-(6-amino-2,4-dioxo-1,2,3,4-tetrahydro-5-pyrimidinyl)-4-[(2-methyl-4-quinolinyl)methoxy]benzenesulfonamide trifluoroacetate Following a procedure analogous to that used in Example 2, but using 5,6-diaminouracil, the product was prepared and purified by HPLC on a C-18 column eluting with an acetonitrile: water: TFA gradient to give the title compound (0.012 g, 19%) as a white amorphous solid. MS found: (M+H)$^+$=454.

Example 5

2,4-dioxo-1,2,3,4-tetrahydro-5-pyrimidinyl 4-[(2-methyl-4-quinolinyl)methoxy]benzenesulfonate trifluoroacetate Following a procedure analogous to that used in Example 2, but using isobarbituric acid, title compound was prepared and purified by HPLC on a C-18 column eluting with an acetonitrile: water: TFA gradient to give the title compound (0.038 g, 60%) as a white amorphous solid. MS found: (M+H)$^+$=440.

Example 6

N-(2,4-dioxo-1,2,3,4-tetrahydro-5-pyrimidinyl)-4-[(2-methyl-4-quinolinyl)methoxy]benzamide trifluoroacetate Following a procedure analogous to that used in Example 2, but using 4-[(2-methyl-4-quinolinyl)methoxy]benzoyl chloride, the product was prepared and purified by HPLC on a C-18 column eluting with an acetonitrile: water: TFA gradient to give the title compound (0.015 g, 9%) as a white amorphous solid. MS found: (M+H)$^+$=403.

Example 7

N-(2,4-dioxohexahydro-5-pyrimidinyl)-4-[(2-methyl-4-quinolinyl)methoxy]benzenesulfonamide trifluoroacetate (7a) A suspension of 5-aminouracil (0.3 g, 2.3 mmol) in ethanol: water (25:5 ml) was degassed with nitrogen gas, then palladium hydroxide on carbon was added. The reaction was charged with hydrogen (65 PSI). The reaction was shaken for 5 h, filtered to remove the catalyst and concentrated to give 5-aminodihydro-2,4(1H,3H)-pyrimidinedione (0.3 g, 100%) as a white solid. MS found: $(M+H)^+=130$.

(7b) Water saturated with sodium bicarbonate (0.5 ml) was added to a suspension of the 5-aminodihydro-2,4(1H,3H)-pyrimidinedione (0.05 g, 0.21 mmol) from step (7a) and 4-[(2-methyl-4-quinolinyl)methoxy]benzenesulfonyl chloride (0.05 g, 0.14 mmol) from step (2b) in dioxane (3 ml) under a nitrogen atmosphere at room temperature. The reaction was stirred for 48 h, concentrated in vacuo, the residue taken up in DMSO (1 ml) and made acidic with TFA. The crude product was purified by HPLC on a C-18 column eluting with an acetonitrile: water: TFA gradient to give the title compound (0.032 g, 48%) as a white amorphous solid. MS found: .$(M+H)^+=441$.

Example 8

N-(2,4-dioxohexahydro-5-pyrimidinyl)-4-[(2-methyl-4-quinolinyl)methoxy]benzamide trifluoroacetate Following a procedure analogous to that used in (7b), but using 4-[(2-methyl-4-quinolinyl)methoxy]benzoyl chloride, the product was prepared and purified by HPLC on a C-18 column eluting with an acetonitrile: water: TFA gradient to give the title compound (0.052 g, 61%) as a white amorphous solid. MS found: $(M+H)^+=405$.

Example 9

6-[({4-[(2-methyl-4-quinolinyl)methoxy]phenyl}thio)methyl]-2,4(1H,3H)-pyrimidinedione trifluoroacetate (9a) Cesium carbonate (1.95 g, 6.0 mmol) was added to a solution of (6-chloromethyl)uracil (0.32 g, 2.0 mmol) and 4-mercaptophenol (0.25 g, 2.0 mmol) in DMSO (3 ml) under a nitrogen atmosphere at room temperature. The reaction was stirred for 1.5 h, diluted with water and pH adjusted to pH=8 with TFA. The aqueous layer was extracted with ethyl acetate (3×). The combined organic layer was washed with brine, dried over magnesium sulfate and concentrated in vacuo to the crude product. The product was purified by HPLC on a C-18 column eluting with an acetonitrile: water: TFA gradient to give 5-{[(4-hydroxyphenyl)thio]methyl}-2,4(1H,3H)-pyrimidinedione (0.314 g, 63%) as a white amorphous solid. MS found: $(M+H)^+=251$.

(9b) Cesium carbonate (0.25 g, 0.77 mmol) was added to a solution of 5-{[(4-hydroxyphenyl)thio]methyl}-2,4 (1H,3H)-pyrimidinedione (0.05 g, 0.2 mmol) from Step (9a) and 4-chloromethyl-2-methylquinoline (0.05 g, 0.26 mmol) in DMSO (1 ml) under a nitrogen atmosphere at room temperature. The reaction was stirred for 5 h, was concentrated in vacuo and purified by HPLC on a C-18 column eluting with an acetonitrile: water: TFA gradient to give the title compound (0.024 g, 23%) as a white amorphous solid. MS found: $(M+H)^+=406$.

Example 10

6-[({4-[(2-methyl-4-quinolinyl)methoxy]phenyl}sulfonyl)methyl]-2,4 (1H,3H)-pyrimidinedione trifluoroacetate Oxone® (0.56 g, 0.92 mmol) dissolved in water (1.5 ml) was added to a suspension of 6-[({4-[(2-methyl-4-quinolinyl)methoxy]phenyl}thio)methyl]-2,4 (1H,3H)-pyrimidinedione trifluoroacetate (0.060 g, 0.116 mmol) from step (9b) in methanol (3 ml) at 0° C. The reaction was stirred for 1.5 h and then allowed to warm to room temperature and stirred an additional 3.5 h. The reaction was concentrated in vacuo to remove the methanol, then was neutralized with 1 N NaOH. The aqueous layer was extracted with ethyl acetate (3×). The combined organic layer was dried over magnesium sulfate, concentrated in vacuo and purified by HPLC on a C-18 column eluting with an acetonitrile: water: TFA gradient to give the title compound (0.025 g, 39%) as a white amorphous solid. MS found: $(M+H)^+=438$.

Example 11

N-[(2,4-dioxo-1,2,3,4-tetrahydro-5-pyrimidinyl)methyl]-4-[(2-methyl-4-quinolinyl)methoxy]benzenesulfonamide trifluoroacetate (11a) A mixture of uracil (3.6 g, 32.1 mmol), formaldehyde (37% in water) (3.25 ml), KOH (1.4 g, 25 mmol) in water (45 ml) was stirred at 50° C. for 20 h. The reaction was acidified with 1 N HCl to give a white precipitate. The solids were collected dried under vacuum to give the 5-(hydroxymethyl)-2,4(1H,3H)-pyrimidinedione (2.01 g, 44%) as a white solid.

(11b) Thionyl chloride ((10 ml) was added to a suspension of 5-(hydroxymethyl)-2,4(1H,3H)-pyrimidinedione (0.60 g, 4.2 mmol)from step (11a) in dioxane (15 ml). The reaction was heated to reflux for 4 h, allowed to cool, and concentrated in vacuo to give the 5-(chloromethyl)-2,4(1H,3H)-pyrimidinedione (0.62 g, 100%) as a yellow solid.

(11c) Sodium azide (0.6 g, 9.34 mmol) was added to a solution of 5-(chloromethyl)-2,4(1H,3H)-pyrimidinedione (0.3 g, 1.67 mmol) in DMSO (5 ml) under nitrogen at room temperature. The reaction was stirred for 2 h then partitioned between ethyl acetate and water. The organic layer was washed with brine, dried over magnesium sulfate and concentrated to give the 5-(azidomethyl)-2,4(1H,3H)-pyrimidinedione (0.275 g, 98%) as a yellow solid.

(11d) The solution of 5-(azidomethyl)-2,4(1H,3H)-pyrimidinedione (0.275 g, 1.64 mmol) in ethanol: water (25:5 ml) was degassed with nitrogen, palladium on carbon (5%) was added, reaction was charged with hydrogen (55 PSI) and shaken for 2 h. The reaction was filtered and concentrated to give the 5-(aminomethyl)-2,4(1H,3H)-pyrimidinedione (0.20 g, 85%) as a solid. MS found: $(M+H)^+=142$.

(11e) Following a procedure analogous to that used in example (2c), but using 5-(aminomethyl)-2,4(1H,3H)-pyrimidinedione from step (11d), the product was prepared and purified by HPLC on a C-18 column eluting with an acetonitrile: water: TFA gradient to give the title compound (0.0035 g, 4%) as a white amorphous solid. MS found: $(M+H)^+=453$.

Example 12

N-[(2,4-dioxo-1,2,3,4-tetrahydro-5-pyrimidinyl)methyl]-4-[(2-methyl-4-quinolinyl)methoxy]benzamide trifluoroacetate Following a procedure analogous to that used in (2c), but using 4-[(2-methyl-4-quinolinyl)methoxy]benzoyl chloride and 5-aminomethyluracil from step (11d), the product was prepared and purified by HPLC on a C-18 column eluting with an acetonitrile: water: TFA gradient to give the title compound (0.0095 g, 13%) as a white amorphous solid. MS found: $(M+H)^+=417$.

Example 13

6-({4-[(2-methyl-4-quinolinyl)methoxy]phenyl}thio)-2,4(1H,3H)-pyrimidinedione trifluoroacetate (13a) A mixture of 4-chlorouracil (0.87 g, 6.0 mmol), 4-mercaptophenol(0.834 g, 6.6 mmol) and KOH (0.435 g, 6.6 mmol) in ethanol (36 ml) was heated to reflux for 24 h. The reaction was allowed to cool, was concentrated in vacuo, and acidified with 1 n HCl. The solids were collected, washed with water and dried to give 6-[(4-hydroxyphenyl)thio]-2,4(1H,3H)-pyrimidinedione (1.1 g, 80%) as a white solid.

(13b) Following a procedure analogous to that used in example (9b), but using the 6-[(4-hydroxyphenyl)thio]-2,4(1H,3H)-pyrimidinedione (0.20 g, 0.85 mmol) from Step (13a) and 4-chloromethyl-2-methylquinoline (0.18 g, 0.98 mmol), the product was prepared and purified by HPLC on a C-18 column eluting with an acetonitrile: water: TFA gradient to give the title compound(0.119 g, 28%) as a white amorphous solid. MS found: $(M+H)^+=392$.

Example 14

N-(2,4-dioxo-1,2,3,4-tetrahydro-5-pyrimidinyl)-4-phenoxybenzenesulfonamide

Following a procedure analogous to that used in (2c), but using 4-phenoxybenzenesulphonyl chloride and 5-aminouracil, the product was prepared and purified by HPLC on a C-18 column eluting with an acetonitrile: water: TFA gradient to give the title compound (0.085 g, 30%) as a white amorphous solid. MS found: $(M-H)^+=358$.

Tables 1–3 below provide representative Examples, the synthesis of which is described above, of the compounds of the present invention.

TABLE 1

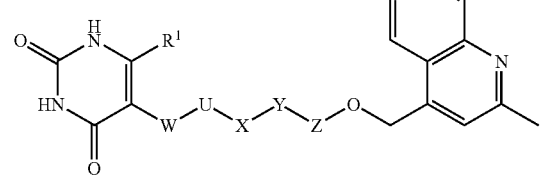

| Ex | $R^1$ | W—U—X—Y | Z | MS [M + H] |
|---|---|---|---|---|
| 2 | H | —NHSO$_2$— | 1,4-phenylene | 439 |
| 3 | H | —NHSO$_2$— | 2,6-naphthylene | 489 |
| 4 | NH$_2$ | —NHSO$_2$— | 1,4-phenylene | 454 |

TABLE 1-continued

| Ex | $R^1$ | W—U—X—Y | Z | MS [M + H] |
|---|---|---|---|---|
| 5 | H | —OSO$_2$— | 1,4-phenylene | 440 |
| 6 | H | —NHCO— | 1,4-phenylene | 403 |
| 9 | H | —CH$_2$S— | 1,4-phenylene | 406 |
| 10 | H | —CH$_2$SO$_2$— | 1,4-phenylene | 438 |
| 11 | H | —CH$_2$NHSO$_2$— | 1,4-phenylene | 453 |
| 12 | H | —CH$_2$NHCO— | 1,4-phenylene | 417 |
| 13 | H | —S— | 1,4-phenylene | 392 |

TABLE 2

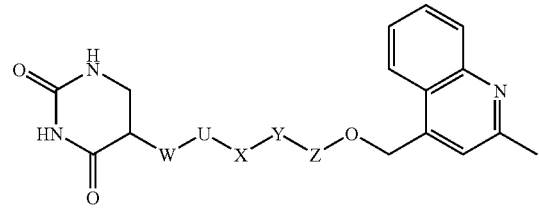

| Ex | W—U—X—Y | Z | MS [M + H] |
|---|---|---|---|
| 7 | —NHSO$_2$— | 1,4-phenylene | 441 |
| 8 | —NHCO— | 1,4-phenylene | 405 |

TABLE 3

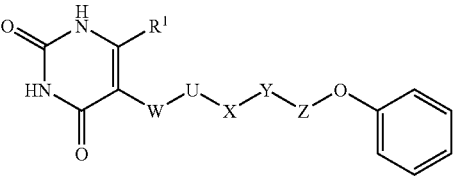

| Ex | $R^1$ | W—U—X—Y | Z | MS [M + H] |
|---|---|---|---|---|
| 14 | H | —NHSO$_2$— | 1,4-phenylene | 358 |

Utility

The compounds of formula I are expected to possess matrix metalloproteinase and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloproteinase-mediated breakdown of cartilage and bone that occurs in osteoporosis patients.

Compounds that inhibit the production or action of TACE and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

The compounds of the present invention can be administered alone or in combination with one or more additional anti-inflammatory agents. These agents include, but are not limited to, selective COX-2 inhibitors, interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denote agents that selectively inhibit COX-2 function. Such agents include, but are not limited to, celecoxib (Celebrex®), rofecoxib (Vioxx®), meloxicam (Movicox®) etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel®), infliximab (Remicade®), adalimumab (D2E7), CDP-571 (Humicade®), and CDP-870.

Other anti-inflammatory agents that may be used in combination with the compounds of this invention, include, but are not limited to, methotrexate, interleukin-1 antagonists (e.g., anakinra (Kineret®)), dihydroorotate synthase inhibitors (e.g., leflunomide (Arava®)), and p38 MAP kinase inhibitors.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention can be used for making a coating on an implantable medical device, more particularly, on a stent, is particularly advantageous in reducing the restinosis or thrombosis associated with introduction of the stent into the mammalian body.

Besides the TACE inhibitor, one or more additional therapeutic agents may be incorporated into the stent coating to provide an additive or synergistic therapeutic advantage. For example, such additional therapeutic agents include, but not limited to: antiproliferative/antimitotic agents including natural 12 products such as vinca alkaloids (i.e., vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L asparagine and deprives cells which don't have the capacity to synthesize their own asparagine); antiproliferative/antimitotic alkylating agents such as nitrogen mustards(mechlorethamine, cyclophosphamide and analogs, melphalan, chlorambucil), ethylenimines and methylmelamines (hexamethylmelamine and thiotepa), alkyl sulfonates—busulfan, nirtosoureas (carmustine (BCNU) and is analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2 chlorodeoxyadenosine(cladribine)); platinum coordination complexes (cisplatin, carboplatin), procarbazine, hydroxyurea, mitotane, aminoglutethimide; hormones (i.e.estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisclone, 6(x methylprednisolone, triamcinolone, betamethasone, and dexamethasone), non-steroidal agents (salicylic acid 13 derivatives i.e., aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); Angiogenic agents: vascular endothelial growth factor (VEGF), fibroblast growth factor (FGF); nitric oxide donors; cell cycle inhibitors; mTOR inhibitors; growth factor signal transduction knase inhibitors; anti sense oligonucleotide; prodrug molecules; and combinations thereof.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma stands for the Sigma-Aldrich Corp. of St. Louis, Mo.

A compound is considered to be active if it has an $IC_{50}$ or $K_i$ value of less than about 10 µM for the inhibition of a desired MP. Preferred compounds of the present invention have $K_i$'s or $IC_{50}$'s of $\leq 1$ µM. More preferred compounds of the present invention have $K_i$'s or $IC_{50}$'s of $\leq 0.1$ µM. Even more preferred compounds of the present invention have $K_i$'s or $TC_{50}$'s of $\leq 0.01$ µM. Still more preferred compounds of the present invention have $K_i$'s or $IC_{50}$'s of $\leq 0.001$ µM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et al. Trans. Ortho. Res. Soc. 1995, 20, 341). Therefore, in order to accumulate BNC aggrecanase in culture media, cartilage is first depleted of endogenous aggrecan by stimulation with 500 mg/mL human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C. E. et al., Biochem. J. 1995, 306, 799–804). This antibody recognizes aggrecan fragments with the N-terminus, 374ARGSVTL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 µM for aggrecanase.

To evaluate inhibition of aggrecanase, compounds are prepared as 10 mM stocks in DMSO, water or other solvents and diluted to appropriate concentrations in water. Drug (50 µL) is added to 50 µL of aggrecanase-containing media and 50 µL of 2 mg/mL aggrecan substrate and brought to a final volume of 200 µL in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 µl of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

TNF PBMC Assay

Human peripheral blood mononuclear cells (PBMC) were obtained from normal donor blood by leukophoresis and isolated by Ficoll-Paque density separation. PBMCs were suspended in 0.5 mL RPMI 1640 with no serum at $2 \times 10^6$ cells/mL in 96 well polystyrene plates. Cells were preincubated 10 minutes with compound, then stimulated with 1 µg/mL LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 µl of blood is plated directly into sterile polypropylene tubes. Compounds are diluted in DMSO/serum free media and added to the blood samples so the final concentration of compounds are 50, 10, 5, 1, 0.5, 0.1, and 0.01 µM. The final concentration of DMSO does not exceed 0.5%. Compounds are preincubated for 15 minutes before the addition of 100 mg/mL LPS. Plates are incubated for 5 hours in an atmosphere of 5% $CO_2$ in air. At the end of 5 hours, 750 µl of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

TNF Induction in Mice

Test compounds are administered to mice either I.P. or P.O. at time zero. Immediately following compound administration, mice receive an I.P. injection of 20 mg of D-galactosamine plus 10 µg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 µM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibition, the $IC_{50}$ values were converted to Ki values as previously described.

Compounds tested in the above assay are considered to be active if they exhibit a $K_i$ of $\leq 10$ µM. Preferred compounds of the present invention have $K_i$'s of $\leq 1$ µM. More preferred compounds of the present invention have $K_i$'s of $\leq 0.1$ µM. Even more preferred compounds of the present invention have $K_i$'s of $\leq 0.01$ µM. Still more preferred compounds of the present invention have $K_i$'s of $\leq 0.001$ µM.

Using the methodology described above, a number of compounds of the present invention were found to exhibit $K_i$'s of $\leq 10$ µM, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an $OR^{a1}$, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any $OR^{a1}$, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

What is claimed is:
1. A compound of formula I:

A-W-U-X-Y-Z-U$^a$-X$^a$-Y$^a$-Z$^a$     I or a stereoisomer or pharmaceutically acceptable salt form thereof, wherein;

A is selected from the group:

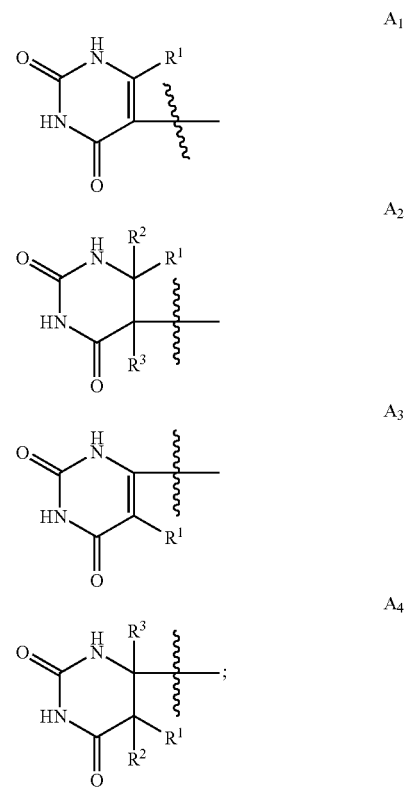

W is (CHR$^a$) m;
U is absent or is selected from: NR$^{a1}$, C(O)NR$^{a1}$, NR$^{a1}$C(O), NR$^{a1}$C(O)O, OS(O)$_2$, S(O)$_2$O, S(O)$_p$, S(O)$_p$NR$^{a1}$, and NR$^{a1}$S (O)$_p$;
X is absent or is selected from C$_{1-3}$ alkylene, C$_{2-3}$ alkenylene, and C$_{2-3}$ alkynylene;
Y is absent or is selected from O, NR$^{a1}$, S(O)$_p$ and C(O);
Z is selected from:
    a C$_{3-13}$ carbocycle substituted with 0–5 R$^b$; and
    a 5–14 membered heterocycle comprising carbon atoms and 1–4 heteroatoms selected from the group consisting of N, O, and S(O)$_p$, and substituted with 0–5 R$^b$;
provided that Z is other than 2-oxo-1,4-pyridinylene;
U$^a$ is absent or is selected from: O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, and NR$^{a1}$SO$_2$NR$^{a1}$;
X$^a$ is absent or is selected from C$_{1-10}$ alkylene, C$_{2-10}$ alkenylene, and C$_{2-10}$ alkynylene;
Y$^a$ is absent or is selected from O, NR$^{a1}$, S(O)$_p$, and C(O);
Z$^a$ is selected from H, a C$_{3-13}$ carbocycle substituted with 0–5 R$^c$, and a 5–14 membered heterocycle comprising carbon atoms and 1–4 heteroatoms selected from the group consisting of N, O, and S(O)$_p$, and substituted with 0–5 R$^c$;
provided that U, Y, Z, U$^a$, Y$^a$, and Z$^a$ do not combine to form a N—N, N—O, O—N, O—O, S(O)$_p$—O, O—S(O)$_p$ or S(O)$_p$—S(O)$_p$ group;
R$^1$, at each occurrence, is independently selected from H, CF$_3$, C$_{1-6}$ alkyl substituted with 0–1 R$^b$, C$_{2-6}$ alkenyl substituted with 0–1 R$^b$, C$_{2-6}$ alkynyl substituted with 0–1 R$^b$, (CR$^a$R$^{a1}$)$_s$OR$^{a1}$, (CR$^a$R$^{a1}$)$_r$NR$^a$R$^{a1}$, (CR$^a$R$^{a1}$)$_r$ C(O)NR$^a$R$^{a1}$, (CR$^a$R$^{a1}$)$_r$—C$_{3-10}$ carbocycle substituted with 0–5 R$^d$, and (CR$^a$R$^{a1}$)$_r$-5–10 membered heterocycle comprising carbon atoms and 1–4 heteroatoms selected from the group consisting of N, O, and S(O)$_p$, and substituted with 0–5 R$^d$;

R$^2$, at each occurrence, is independently selected from H, C$_{1-6}$ alkyl substituted with 0–1 R$^b$, C$_{2-6}$ alkenyl substituted with 0–1 R$^b$, and C$_{2-6}$ alkynyl substituted with 0–1 R$^b$;

R$^3$, at each occurrence, is independently selected from H, C$_{1-6}$ alkyl substituted with 0–1 R$^b$, C$_{2-6}$ alkenyl substituted with 0–1 R$^b$, and C$_{2-6}$ alkynyl substituted with 0–1 R$^b$;

R$^a$, at each occurrence, is independently selected from H, C$_{1-6}$ alkyl, phenyl, and benzyl;

R$^{a1}$, at each occurrence, is independently selected from H, C$_{1-6}$ alkyl substituted with 0–1 R$^e$, C$_{2-6}$ alkenyl substituted with 0–1 R$^e$, C$_{2-6}$ alkynyl substituted with 0–1 R$^e$, and —(CH$_2$)$_r$-3–8 membered carbocyclic or heterocyclic ring comprising carbon atoms and 0–2 ring heteroatoms selected from N, NR$^{a2}$, O, and S(O)$_p$ and substituted with 0–3 R$^e$;

alternatively, R$^a$ and R$^{a1}$, when attached to a nitrogen, are taken together with the nitrogen to which they are attached form a 5 or 6 membered heterocycle comprising carbon atoms and from 0–1 additional heteroatoms selected from N, NR$^{a2}$, O, and S(O)$_p$;

R$^{a2}$, at each occurrence, is independently selected from C$_{1-4}$ alkyl, phenyl, and benzyl;

R$^{a3}$, at each occurrence, is independently selected from H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, and —(CH$_2$)$_r$-3–8 membered carbocyclic or heterocyclic ring comprising carbon atoms and 0–2 ring heteroatoms selected from N, NR$^{a2}$, O, and S(O)$_p$, and substituted with 0–3 R$^{c1}$;

R$^b$, at each occurrence, is independently selected from C$_{1-6}$ alkyl substituted with 0–1 R$^{c1}$, OR$^a$, SR$^a$, Cl, F, Br, I, =O, —CN, NO$_2$, NR$^a$R$^{a1}$, C(O)R$^a$, C(O)OR$^a$, C(O)NR$^a$R$^{a1}$, C(S)NR$^a$R$^{a1}$, NR$^a$C(O)NR$^a$R$^{a1}$, OC(O)NR$^a$R$^{a1}$, NR$^a$C(O)OR$^a$, S(O)$_2$NR$^a$R$^{a1}$, NR$^a$S(O)$_2$R$^{a3}$, NR$^a$S(O)$_2$NR$^a$R$^{a1}$, OS(O)$_2$NR$^a$R$^{a1}$, NR$^a$S(O)$_2$R$^{a3}$, S(O)$_p$R$^{a3}$, CF$_3$, CF$_2$CF$_3$, CHF$_2$, CH$_2$F, and phenyl;

R$^c$, at each occurrence, is independently selected from H, OR$^a$, Cl, F, Br, I, =O, —CN, NO$_2$, CF$_3$, CF$_2$CF$_3$, OCF$_3$, (CR$^a$R$^{a1}$)$_r$NR$^a$R$^{a1}$, (CR$^a$R$^{a1}$)$_r$C(=NCN)NR$^a$R$^{a1}$, (CR$^a$R$^{a1}$)$_r$C(=NR$^a$)NR$^a$R$^{a1}$, (CR$^a$R$^{a1}$)$_r$C(=NOR$^a$)NR$^a$R$^{a1}$, (CR$^a$R$^{a1}$)$_r$C(O)NR$^a$OH, (CR$^a$R$^{a1}$)$_r$C(O)R$^a$, (CR$^a$R$^{a1}$)$_r$C(O)OR$^{a1}$, (CR$^a$R$^{a1}$)$_r$C(S)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$C(S)NR$^a$R$^{a1}$, (CR$^a$R$^{a1}$)$_r$OC(O)NR$^a$R$^{a1}$, (CR$^a$R$^{a1}$)$_r$NR$^a$C(O)OR$^{a1}$, (CR$^a$R$^{a1}$)$_r$NR$^a$C(O)NR$^a$R$^{a1}$, (CR$^a$R$^{a1}$)$_r$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$, (CR$^a$R$^{a1}$)$_r$NR$^a$SO$_2$NR$^a$R$^{a1}$;

C$_{1-6}$ alkyl substituted with 0–2 R$^{c1}$;
C$_{2-6}$ alkenyl substituted with 0–2 R$^{c1}$;
C$_{2-6}$ alkynyl substituted with 0–2 R$^{c1}$;
(CR$^a$R$^{a1}$)$_r$—C$_{3-10}$ carbocycle substituted with 0–2 R$^{c1}$; and
(CR$^a$R$^{a1}$)$_r$-5–14 membered heterocycle comprising carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a spiro ring C that is a 3–11 membered carbocycle or heterocycle substituted with 0–2 R$^{c1}$ and comprising: carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^{c1}$, at each occurrence, is independently selected from H, C$_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)OR$^{a1}$, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, OCF$_3$, CF$_2$CF$_3$, CH$_2$F, and CHF$_2$;

R$^d$, at each occurrence, is independently selected from C$_{1-6}$ alkyl substituted with 0–2 R$^e$, C$_{2-6}$ alkenyl, C$_{2-6}$ alkynyl, OR$^a$, Cl, F, Br, I, =O, —CN, NO$_2$, NR$^a$R$^{a1}$, C(O)R$^{a1}$, C(O)OR$^a$, C(O)NR$^a$R$^{a1}$, C(S)NR$^a$R$^{a1}$, R$^a$NC(O)NR$^a$R$^{a1}$, OC(O)NR$^a$R$^{a1}$, R$^a$NC(O)OR$^{a1}$, S(O)$_2$NR$^a$R$^{a1}$, NR$^a$S(O)$_2$R$^{a3}$, NR$^a$S(O)$_2$NR$^a$R$^{a1}$, OS(O)$_2$NR$^a$R$^{a1}$, NR$^a$S(O)$_2$R$^{a3}$, S(O)$_p$R$^{a3}$, CF$_3$, and CF$_2$CF$_3$;

R$^e$, at each occurrence, is independently selected from H, C$_{1-6}$ alkyl, OR$^a$, Cl, F, Br, I, =O, —CN, NO$_2$, NR$^a$R$^a$, C(O)R$^a$, C(O)OR$^a$, C(O)NR$^a$R$^a$, R$^a$NC(O)NR$^a$R$^a$, OC(O)NR$^a$R$^a$, R$^a$NC(O)OR$^a$, S(O)$_2$NR$^a$R$^a$, NR$^a$S(O)$_2$R$^{a2}$, NR$^a$S(O)$_2$NR$^a$R$^a$, OS(O)$_2$NR$^a$R$^a$, NR$^a$S(O)$_2$R$^{a2}$, S(O)$_p$R$^{a2}$, CF$_3$, OCF$_3$, CF$_2$CF$_3$, CH$_2$F, and CHF$_2$;

m, at each occurrence, is selected from 0, 1, 2 and 3;
p, at each occurrence, is selected from 0, 1, and 2;
r, at each occurrence, is selected from 0, 1, 2, 3, and 4;
s, at each occurrence, is selected from 1, 2, 3, and 4; and
provided that
  i) when Z is phenylene or naphthylene, then U$^a$-X$^a$-Y$^a$-Z$^a$ forms a group other than H, C$_{1-6}$ alkyl, NH$_2$, NHCOCH$_3$, or naphthyl;
  ii) when W-U-X-Y forms —NHSO$_2$—, Z is naphthylene, then Z$^a$ is a group other than phenyl substituted with 0–5 R$^c$;
  iii) when W-U-X-Y forms —NHSO$_2$—, Z is phenylene, U$^a$-X$^a$-Y$^a$ forms a bond, then Z$^a$ is a group other than phenyl substituted with 0–5 R$^c$;
  iv) when W-U-X-Y forms —NR$^{a1}$SO$_2$—, Z is phenylene, then Z$^a$ is a group other than phenyl substituted with one 5–6 membered carbocycle or heterocycle substituted with 0–2 R$^{c1}$;
  v) when R$^1$ is (CR$^a$R$^{a1}$)$_r$NR$^a$R$^{a1}$ or (CR$^a$R$^{a1}$)$_r$C(O)NR$^a$R$^{a1}$, Z is phenylene or naphthylene, then U$^a$-X$^a$-Y$^a$ forms a group other than a bond and Z$^a$ is other than H; and
  vi) when W-U-X-Y forms —NHSO$_2$CH$_2$— or —NHCOCH$_2$—, Z is naphthyl, then U$^a$-X$^a$-Y$^a$ forms other than CH$_2$CH$_2$NR$^{1a}$.

2. A compound according to claim 1, wherein;
W is (CHR$^a$)$_m$;
U is absent or is selected from: C(O)NR$^{a1}$, NR$^{a1}$C(O), NR$^{a1}$C(O)O, OS(O)$_2$, S(O)$_2$O, S(O)$_2$, S(O)$_p$NR$^{a1}$, and NR$^{a1}$S(O)$_p$;
X is absent or is C$_{1-3}$ alkylene;
Y is absent;
U$^a$ is absent or is selected from: O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$_{a1}$, NR$^{a1}$S(O)$_p$, and NR$^{a1}$SO$_2$NR$^{a1}$;

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{3-13}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that U, Y, Z, $U^a$, $Y^a$, and $Z^a$ do not combine to form a N—N, N—O, O—N, O—O, $S(O)_p$—O, O—S$(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, $C_{2-6}$ alkynyl substituted with 0–1 $R^b$, $(CR^aR^{a1})_sOR^{a1}$, $(CR^aR^{a1})_rNR^aR^{a1}$, $(CR^aR^{a1})_r$C(O)$NR^aR^{a1}$, $(CR^aR^{a1})_r$—$C_{3-10}$ carbocycle substituted with 0–3 $R^d$, and $(CR^aR^{a1})_r$-5–10 membered heterocycle comprising carbon atoms and 1–4 heteroatoms selected from the group consisting of N, O, and $S(O)_p$, and substituted with 0–3 $R^d$;

$R^2$, at each occurrence, is independently selected from H, $C_{1-6}$ alkyl, $C_{2-6}$ alkenyl, and $C_{2-6}$ alkynyl;

$R^3$, at each occurrence, is independently selected from H, $C_{1-6}$ alkyl, $C_{2-6}$ alkenyl, and $C_{2-6}$ alkynyl;

$R^a$, at each occurrence, is independently selected from H, $C_{1-6}$ alkyl, phenyl, and benzyl;

$R^{a1}$, at each occurrence, is independently selected from H, $C_{1-6}$ alkyl, phenyl, and benzyl;

$R^{a3}$, at each occurrence, is independently selected from H, $C_{1-4}$ alkyl, phenyl, and benzyl; and $R^c$, at each occurrence, is independently selected from H, $OR^a$, Cl, F, Br, =O, —CN, $NO_2$, $NR^aR^{a1}$, $CF_3$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_sS(O)_pR^{a3}$, $(CR^aR^{a1})_sSO_2NR^aR^{a1}$, $(CR^aR^{a1})_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and $(CH_2)_r$-5–6 membered heterocycle comprising carbon atoms and 1–4 heteroatoms selected from the group consisting of N, O, and $S(O)_p$, and substituted with 0–2 $R^{c1}$.

3. A compound according to claim 2, wherein;

W is absent or is $CH_2$;

U is selected from: C(O)NH, NHC(O), OS(O)$_2$, S(O)$_2$O, S(O)$_2$, S(O)$_2$NH, and NHS(O)$_2$;

X is absent;

Y is absent;

Z is selected from:

phenylene substituted with 0–5 $R^b$;

naphthylene substituted with 0–5 $R^b$; and a 5–14 membered heterocycle comprising carbon atoms and 1–4 heteroatoms selected from the group consisting of N, O, and $S(O)_p$, and substituted with 0–5 $R^b$;

$U^a$ is absent or is selected from: O, $NR^{a1}$, and $CR^a$(OH);

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{5-10}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that U, Y, Z, $U^a$, $Y^a$, and $Z^a$ do not combine to form a N—N, N—O, O—N, O—O, $S(O)_p$—O, O—S$(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_nOR^{a1}$, and $(CH_2)_rNR^aR^{a1}$;

$R^2$, at each occurrence, is independently selected from H and $C_{1-4}$ alkyl;

$R^3$, at each occurrence, is independently selected from H and $C_{1-4}$ alkyl;

$R^a$, at each occurrence, is independently selected from H and $C_{1-6}$ alkyl;

$R^{a1}$, at each occurrence, is independently selected from H and $C_{1-6}$ alkyl;

$R^{a3}$, at each occurrence, is independently selected from H, $C_{1-4}$ alkyl, phenyl, and benzyl; and $R^c$, at each occurrence, is independently selected from H, $OR^a$, Cl, F, Br, =O, —CN, $NO_2$, $NR^aR^{a1}$, $CF_3$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_sSO_2NR^aR^{a1}$, $(CR^aR^{a1})_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and $(CH_2)_r$-5–6 membered heterocycle comprising carbon atoms and 1–4 heteroatoms selected from the group consisting of N, O, and $S(O)_p$, and substituted with 0–2 $R^{c1}$.

4. A compound according to claim 3, wherein;

W is absent or is $CH_2$;

U is selected from: NHC(O), OS(O)$_2$, S(O)$_2$, and NHS(O)$_2$;

X is absent;

Y is absent;

Z is selected from:

phenylene substituted with 0–5 $R^b$; and naphthylene substituted with 0–5 $R^b$;

$U^a$ is absent or is O;

$X^a$ is absent or is $CH_2$ or $CH_2CH_2$;

$Y^a$ is absent or is O;

$Z^a$ is a 5–10 membered heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolyl;

provided that U, Y, Z, $U^a$, $Y^a$, and $Z^a$ do not combine to form a N—N, N—O, O—N, O—O, $S(O)_p$—O, O—S$(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_sOR^{a1}$, and $(CH_2)_rNR^aR^{a1}$; and $R^c$, at each occurrence, is independently selected from H, $OR^a$, Cl, F, Br, =O, —CN, $NO_2$, $NR^aR^{a1}$, $CF_3$, $(CH_2)_rC(O)R^{a1}$, $(CH_2)_rC(O)OR^{a1}$, $(CH_2)_rC(O)NR^aR^{a1}$, $(CH_2)_rNR^aC(O)R^{a1}$, $(CH_2)_sS(O)_pR^{a3}$, $(CH_2)_rSO_2NR^aR^{a1}$, $(CH_2)_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and (CH$_2$)$_r$-5–6 membered heterocycle comprising carbon atoms and 1–4 heteroatoms selected from the group consisting of N, O, and S(O)$_p$, and substituted with 0–2 R$^{c1}$.

5. A compound according to claim 1, wherein the compound is of formula Ia:

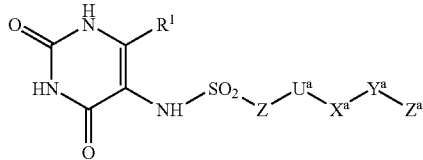

or a stereoisomer or pharmaceutically acceptable salt form thereof, wherein;

Z is selected from:
  a C$_{3-13}$ carbocycle substituted with 0–5 R$^b$; and
  a 5–14 membered heterocycle comprising carbon atoms and 1–4 heteroatoms selected from the group consisting of N, O, and S(O)$_p$, and substituted with 0–5 R$^b$;
provided that Z is other than 2-oxo-1,4-pyridinylene;

U$^a$ is absent or is selected from: O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, and NR$^{a1}$SO$_2$NR$^{a1}$;

X$^a$ is absent or is selected from C$_{1-10}$ alkylene, C$_{2-10}$ alkenylene, and C$_{2-10}$ alkynylene;

Y$^a$ is absent or is selected from O, NR$^{a1}$, S(O)$_p$, and C(O);

Z$^a$ is selected from H, a C$_{3-13}$ carbocycle substituted with 0–5 R$^c$, and a 5–14 membered heterocycle comprising carbon atoms and 1–4 heteroatoms selected from the group consisting of N, O, and S(O)$_p$, and substituted with 0–5 R$^c$;

provided that U, Y, Z, U$^a$, Y$^a$, and Z$^a$ do not combine to form a N—N, N—O, O—N, O—O, S(O)$_p$—O, O—S(O)$_p$ or S(O)$_p$—S(O)$_p$ group;

R$^1$, at each occurrence, is independently selected from H, CF$_3$, C$_{1-6}$ alkyl substituted with 0–1 R$^b$, C$_{2-6}$ alkenyl substituted with 0–1 R$^b$, C$_{2-6}$ alkynyl substituted with 0–1 R$^b$, (CR$^a$R$^{a1}$)$_s$OR$^{a1}$, (CR$^a$R$^{a1}$)$_r$NR$^a$R$^{a1}$, (CR$^a$R$^{a1}$)$_r$C(O)NR$^a$R$^{a1}$, (CR$^a$R$^{a1}$)$_r$—C$_{3-10}$ carbocycle substituted with 0–5 R$^d$, and (CR$^a$R$^{a1}$)$_r$-5–1 membered heterocycle comprising carbon atoms and 1–4 heteroatoms selected from the group consisting of N, O, and S(O)$_p$, and substituted with 0–5 R$^d$;

R$^a$, at each occurrence, is independently selected from H, C$_{1-6}$ alkyl, phenyl, and benzyl;

R$^{a1}$, at each occurrence, is independently selected from H, C$_{1-6}$ alkyl substituted with 0–1 R$^e$, C$_{2-6}$ alkenyl substituted with 0–1 R$^e$, C$_{2-6}$ alkynyl substituted with 0–1 R$^e$, and —(CH$_2$)$_r$-3–8 carbocyclic or heterocyclic ring comprising carbon atoms and 0–2 ring heteroatoms selected from N, NR$^{a2}$, O, and S(O)$_p$, and substituted with 0–3 R$^e$;

alternatively, R$^a$ and R$^{a1}$, when attached to a nitrogen, are taken together with the nitrogen to which they are attached form a 5 or 6 membered heterocycle comprising carbon atoms and from 0–1 additional heteroatoms selected from N, NR$^{a2}$, O, and S(O)$_p$;

R$^{a2}$, at each occurrence, is independently selected from C$_{1-4}$ alkyl, phenyl, and benzyl;

R$^{a3}$, at each occurrence, is independently selected from H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, and —(CH$_2$)$_r$-3–8 membered carbocyclic or heterocyclic ring comprising carbon atoms and 0–2 ring heteroatoms selected from N, NR$^{a2}$, O, and S(O)$_p$, and substituted with 0–3 R$^{c1}$;

R$^b$, at each occurrence, is independently selected from C$_{1-6}$ alkyl substituted with 0–1 R$^{c1}$, OR$^a$, SR$^a$, Cl, F, Br, I, =O, —CN, NO$_2$, NR$^a$R$^{a1}$, C(O)R$^a$, C(O)OR$^a$, C(O)NR$^a$R$^{a1}$, C(S)NR$^a$R$^{a1}$, NR$^a$C(O)NR$^a$R$^{a1}$, OC(O)NR$^a$R$^{a1}$, NR$^a$C(O)OR$^a$, S(O)$_2$NR$^a$R$^{a1}$, NR$^a$S(O)$_2$R$^{a3}$, NR$^a$S(O)$_2$NR$^a$R$^{a1}$, OS(O)$_2$NR$^a$R$^{a1}$, NR$^a$S(O)$_2$R$^{a3}$, S(O)$_p$R$^{a3}$, CF$_3$, CF$_2$CF$_3$, CHF$_2$, CH$_2$F, and phenyl;

R$^c$, at each occurrence, is independently selected from H, OR$^a$, Cl, F, Br, I, =O, —CN, NO$_2$, CF$_3$, CF$_2$CF$_3$, CH$_2$F, CHF$_2$, CF$_2$CH$_3$, C(CH$_3$)$_2$F, OCF$_3$, (CR$^a$R$^{a1}$)$_r$NR$^a$R$^{a1}$, (CR$^a$R$^{a1}$)$_r$C(=NCN)NR$^a$R$^{a1}$, (CR$^a$R$^{a1}$)$_r$C(=NR$^a$)NR$^a$R$^{a1}$, (CR$^a$R$^{a1}$)$_r$C(=NOR$^a$)NR$^a$R$^{a1}$, (CR$^a$R$^{a1}$)$_r$C(O)NR$^a$OH, (CR$^a$R$^{a1}$)$_r$C(O)R$^{a1}$, (CR$^a$R$^{a1}$)$_r$C(O)OR$^{a1}$, (CR$^a$R$^{a1}$)$_r$C(S)OR$^{a1}$, (CR$^a$R$^{a1}$)$_r$C(O)NR$^a$R$^{a1}$, (CR$^a$R$^{a1}$)$_r$NR$^a$C(O)R$^{a1}$, (CR$^a$R$^{a1}$)$_r$C(S)NR$^a$R$^{a1}$, (CR$^a$R$^{a1}$)$_r$C(O)NR$^a$R$^{a1}$, (CR$^a$R$^{a1}$)$_r$NR$^a$C(O)OR$^{a1}$, (CR$^a$R$^{a1}$)$_r$NR$^a$C(O)NR$^a$R$^{a1}$, (CR$^a$R$^{a1}$)$_r$S(O)$_p$R$^{a3}$, (CR$^a$R$^{a1}$)$_r$SO$_2$NR$^a$R$^{a1}$, (CR$^a$R$^{a1}$)$_r$NR$^a$SO$_2$R$^{a3}$, (CR$^a$R$^{a1}$)$_r$NR$^a$SO$_2$NR$^a$R$^{a1}$;

C$_{1-6}$ alkyl substituted with 0–2 R$^{c1}$;
C$_{2-6}$ alkenyl substituted with 0–2 R$^{c1}$;
C$_{2-6}$ alkynyl substituted with 0–2 R$^{c1}$;
(CR$^a$R$^{a1}$)$_r$—C$_{3-10}$ carbocycle substituted with 0–2 R$^{c1}$; and
(CR$^a$R$^{a1}$)$_r$-5–14 membered heterocycle comprising carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a spiro ring C that is a 3–11 membered carbocycle or heterocycle substituted with 0–2 R$^{c1}$ and comprising: carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

R$^{c1}$, at each occurrence, is independently selected from H, C$_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)OR$^{a1}$, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, OCF$_3$, CF$_2$CF$_3$, CH$_2$F, and CHF$_2$;

R$^d$, at each occurrence, is independently selected from C$_{1-6}$ alkyl substituted with 0–2 R$^e$, C$_{2-6}$ alkenyl, C$_{2-6}$ alkynyl, OR$^a$, Cl, F, Br, I, =O, —CN, NO$_2$, NR$^a$R$^{a1}$, C(O)R$^{a1}$, C(O)OR$^a$, C(O)NR$^a$R$^{a1}$, C(S)NR$^a$R$^{a1}$, R$^a$NC(O)NR$^a$R$^{a1}$, OC(O)NR$^a$R$^{a1}$, R$^a$NC(O)OR$^{a1}$, S(O)$_2$NR$^a$R$^{a1}$, NR$^a$S(O)$_2$R$^{a3}$, NR$^a$S(O)$_2$NR$^a$R$^{a1}$, OS(O)$_2$NR$^a$R$^{a1}$, NR$^a$S(O)$_2$R$^{a3}$, S(O)$_p$R$^{a3}$, CF$_3$, and CF$_2$CF$_3$;

R$^e$, at each occurrence, is independently selected from H, C$_{1-6}$ alkyl, OR$^a$, Cl, F, Br, I, =O, —CN, NO$_2$, NR$^a$R$^a$, C(O)R$^a$, C(O)OR$^a$, C(O)NR$^a$R$^a$, R$^a$NC(O)NR$^a$R$^a$, OC(O)NR$^a$R$^a$, R$^a$NC(O)OR$^a$, S(O)$_2$NR$^a$R$^a$, NR$^a$S(O)$_2$ $R^{a2}$, $NR^aS(O)_2NR^aR^a$, $OS(O)_2NR^aR^a$, $NR^aS(O)_2R^{a2}$, $S(O)_pR^{a2}$, $CF_3$, $OCF_3$, $CF_2CF_3$, $CH_2F$, and $CHF_2$;

p, at each occurrence, is selected from 0, 1, and 2;

r, at each occurrence, is selected from 0, 1, 2, 3, and 4;

s, at each occurrence, is selected from 1, 2, 3, and 4; and provided that i) when Z is phenylene or naphthylene, then $U^a$-$X^a$-$Y^a$-$Z^a$ forms a group other than H, $C_{1-6}$ alkyl, $NH_2$, $NHCOCH_3$, or naphthyl;

ii) when Z is naphthylene, then $Z^a$ is a group other than phenyl substituted with 0–5 $R^c$;

iii) when Z is phenylene, $U^a$-$X^a$-$Y^a$ forms a bond, then $Z^a$ is a group other than phenyl substituted with 0–5 $R^c$;

iv) when Z is phenylene, then $Z^a$ is a group other than phenyl substituted with one 5–6 membered carbocycle or heterocycle substituted with 0–2 $R^{c1}$; and v) when $R^1$ is $(CR^aR^{a1})_rNR^aR^{a1}$ or $(CR^aR^{a1})_rC(O)NR^aR^{a1}$, Z is phenylene or naphthylene, then $U^a$-$X^a$-$Y^a$ forms a group other than a bond and $Z^a$ is other than H.

6. A compound according to claim 5, wherein:

$U^a$ is absent or is selected from: O, $NR^{a1}$, and $CR^a(OH)$;

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{3-13}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, $C_{2-6}$ alkynyl substituted with 0–1 $R^b$, $(CR^aR^{a1})_sOR^{a1}$, $(CR^aR^{a1})_rNR^aR^{a1}$, $(CR^aR^{a1})_rC(O)NR^aR^{a1}$, $(CR^aR^{a1})_r$—$C_{3-10}$ carbocycle substituted with 0–3 $R^d$, and $(CR^aR^{a1})_r$-5–10 membered heterocycle comprising carbon atoms and 1–4 heteroatoms selected from the group consisting of N, O, and $S(O)_p$, and substituted with 0–3 $R^d$;

$R^a$, at each occurrence, is independently selected from H, $C_{1-6}$ alkyl, phenyl, and benzyl;

$R^{a1}$, at each occurrence, is independently selected from H, $C_{1-6}$ alkyl, phenyl, and benzyl;

$R^{a3}$, at each occurrence, is independently selected from H, $C_{1-4}$ alkyl, phenyl, and benzyl;

$R^c$, at each occurrence, is independently selected from H, $OR^a$, Cl, F, Br, =O, —CN, $NO_2$, $NR^aR^{a1}$, $CF_3$, $(CR^aR^{a1})C(O) R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$; and $C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and $(CH_2)_r$-5–6 membered heterocycle comprising carbon atoms and 1–4 heteroatoms selected from the group consisting of N, O, and $S(O)_p$, and substituted with 0–2 $R^{c1}$.

7. A compound according to claim 6, wherein;

Z is selected from:

phenylene substituted with 0–5 $R^b$;

naphthylene substituted with 0–5 $R^b$; and a 5–14 membered heterocycle comprising carbon atoms and 1–4 heteroatoms selected from the group consisting of N, O and $S(O)_p$, and substituted with 0–5 $R^b$;

$U^a$ is absent or is selected from: O, $NR^{a1}$, and $CR^a(OH)$;

$X^a$ is absent or is selected from $C_{1-4}$ alkylene, $C_{2-4}$ alkenylene, and $C_{2-4}$ alkynylene;

$Y^a$ is absent or is selected from O and $NR^{a1}$;

$Z^a$ is selected from a $C_{5-10}$ carbocycle substituted with 0–5 $R^c$, and a 5–14 membered heterocycle comprising carbon atoms and 1–4 heteroatoms selected from the group consisting of N, O, and $S(O)_p$, and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_sOR^{a1}$, and $(CH_2)_rNR^aR^{a1}$;

$R^a$, at each occurrence, is independently selected from H and $C_{1-6}$ alkyl;

$R^{a1}$, at each occurrence, is independently selected from H and $C_{1-6}$ alkyl;

$R^{a3}$, at each occurrence, is independently selected from H, $C_{1-4}$ alkyl, phenyl, and benzyl; and $R^c$, at each occurrence, is independently selected from H, $OR^a$, Cl, F, Br, =O, —CN, $NO_2$, $NR^aR^{a1}$, $CF_3$, $(CR^aR^{a1})_rC(O)R^{a1}$, $(CR^aR^{a1})_rC(O)OR^{a1}$, $(CR^aR^{a1})_rC(O)NR^aR^{a1}$, $(CR^aR^{a1})_rNR^aC(O)R^{a1}$, $(CR^aR^{a1})_rS(O)_pR^{a3}$, $(CR^aR^{a1})_rSO_2NR^aR^{a1}$, $(CR^aR^{a1})_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

$(CH_2)_r$—$C_{3-6}$ carbocycle substituted with 0–2 $R^{c1}$; and $(CH_2)_r$-5–6 membered heterocycle comprising carbon atoms and 1–4 heteroatoms selected from the group consisting of N, O, and $S(O)_p$, and substituted with 0–2 $R^{c1}$.

8. A compound according to claim 7, wherein;

Z is selected from:

phenylene substituted with 0–3 $R^b$; and naphthylene substituted with 0–3 $R^b$;

$U^a$ is absent or is O;

$X^a$ is absent or is $CH_2$ or $CH_2CH_2$;

$Y^a$ is absent or is O;

$Z^a$ is a 5–10 membered heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolyl;

provided that $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$, at each occurrence, is independently selected from H, $CF_3$, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$, $(CH_2)_sOR^{a1}$, and $(CH_2)_rNR^aR^{a1}$; and $R^c$, at each occurrence, is independently selected from H, $OR^a$, Cl, F, Br, =O, —CN, $NO_2$, $NR^aR^{a1}$, $CF_3$, $(CH_2)_rC(O)R^{a1}$, $(CH_2)_rC(O)OR^{a1}$, $(CH_2)_rC(O)NR^aR^{a1}$, $(CH_2)_rNR^aC(O)R^{a1}$, $(CH_2)_rS(O)_pR^{a3}$, $(CH_2)_rSO_2NR^aR^{a1}$, $(CH_2)_rNR^aSO_2R^{a3}$;

$C_{1-6}$ alkyl substituted with 0–1 $R^{c1}$;

$C_{2-6}$ alkenyl substituted with 0–1 $R^{c1}$;

$C_{2-6}$ alkynyl substituted with 0–1 $R^{c1}$;

(CH$_2$)$_r$—C$_{3-6}$ carbocycle substituted with 0–2 R$^{c1}$; and
(CH$_2$)$_r$-5–6 membered heterocycle comprising carbon atoms and 1–4 heteroatoms selected from the group consisting of N, O, and S(O)$_p$, and substituted with 0–2 R$^{c1}$.

9. A compound according to claim 1, wherein the compound is selected from the group:
N-(2,4-dioxo-1,2,3,4-tetrahydro-5-pyrimidinyl)-4-[(2-methyl-4-quinolinyl)methoxy]benzenesulfonamide;
N-(2,4-dioxo-1,2,3,4-tetrahydro-5-pyrimidinyl)-6-[(2-methyl-4-quinolinyl)methoxy]-2-naphthalenesulfonamide;
N-(6-amino-2,4-dioxo-1,2,3,4-tetrahydro-5-pyrimidinyl)-4-[(2-methyl-4-quinolinyl)methoxy]benzenesulfonamide;
2,4-dioxo-1,2,3,4-tetrahydro-5-pyrimidinyl 4-[(2-methyl-4-quinolinyl)methoxy]benzenesulfonate;
N-(2,4-dioxo-1,2,3,4-tetrahydro-5-pyrimidinyl)-4-[(2-methyl-4-quinolinyl)methoxy]benzamide;
N-(2,4-dioxohexahydro-5-pyrimidinyl)-4-[(2-methyl-4-quinolinyl)methoxy]benzenesulfonamide;
N-(2,4-dioxohexahydro-5-pyrimidinyl)-4-[(2-methyl-4-quinolinyl)methoxy]benzamide;
N-[(2,4-dioxo-1,2,3,4-tetrahydro-5-pyrimidinyl)methyl]-4-[(2-methyl-4-quinolinyl)methoxy]benzenesulfonamide;
6-({4-[(2-methyl-4-quinolinyl)methoxy]phenyl}thio)-2,4 (1H,3H)-pyrimidinedione;
N-(2,4-dioxo-1,2,3,4-tetrahydro-5-pyrimidinyl)-4-phenoxybenzenesulfonamide;
or a pharmaceutically acceptable salt form thereof.

10. A pharmaceutical composition, comprising: a pharmaceutically acceptable carrier and a therapeutically effective amount of a compound of claim 1 or a pharmaceutically acceptable salt form thereof.

11. A pharmaceutical composition, comprising: a pharmaceutically acceptable carrier and a therapeutically effective amount of a compound of claim 2 or a pharmaceutically acceptable salt form thereof.

12. A pharmaceutical composition, comprising: a pharmaceutically acceptable carrier and a therapeutically effective amount of a compound of claim 3 or a pharmaceutically acceptable salt form thereof.

13. A pharmaceutical composition, comprising: a pharmaceutically acceptable carrier and a therapeutically effective amount of a compound of claim 4 or a pharmaceutically acceptable salt form thereof.

14. A pharmaceutical composition, comprising: a pharmaceutically acceptable carrier and a therapeutically effective amount of a compound of claim 5 or a pharmaceutically acceptable salt form thereof.

15. A pharmaceutical composition, comprising: a pharmaceutically acceptable carrier and a therapeutically effective amount of a compound of claim 6 or a pharmaceutically acceptable salt form thereof.

16. A pharmaceutical composition, comprising: a pharmaceutically acceptable carrier and a therapeutically effective amount of a compound of claim 7 or a pharmaceutically acceptable salt form thereof.

17. A pharmaceutical composition, comprising: a pharmaceutically acceptable carrier and a therapeutically effective amount of a compound of claim 8 or a pharmaceutically acceptable salt form thereof.

18. A pharmaceutical composition, comprising: a pharmaceutically acceptable carrier and a therapeutically effective amount of a compound of claim 9 or a pharmaceutically acceptable salt form thereof.

* * * * *